(12) United States Patent
Imran

(10) Patent No.: US 8,034,118 B2
(45) Date of Patent: *Oct. 11, 2011

(54) IMPLANTABLE DIGESTIVE TRACT ORGAN

(75) Inventor: Mir A. Imran, Los Altos Hills, CA (US)

(73) Assignee: Python Medical, Inc., Menlo Park, CA (US)

( * ) Notice: Subject to any disclaimer, the term of this patent is extended or adjusted under 35 U.S.C. 154(b) by 585 days.

This patent is subject to a terminal disclaimer.

(21) Appl. No.: 11/549,573

(22) Filed: Oct. 13, 2006

(65) Prior Publication Data

US 2007/0093910 A1 Apr. 26, 2007

Related U.S. Application Data

(63) Continuation of application No. 10/328,446, filed on Dec. 23, 2002, now Pat. No. 7,141,071.

(51) Int. Cl.
*A61F 2/04* (2006.01)

(52) U.S. Cl. .................................. 623/23.64

(58) Field of Classification Search ...... 623/23.64–23.7, 623/11.11; 606/191–192, 151, 157; 600/37, 600/29, 40, 30; 604/96.01
See application file for complete search history.

(56) References Cited

U.S. PATENT DOCUMENTS

| 4,790,313 | A | * | 12/1988 | Borrelly ...................... 128/897 |
| 4,809,676 | A | * | 3/1989 | Freeman ...................... 600/16 |
| 5,116,494 | A | | 5/1992 | Chick et al. |
| 5,261,898 | A | * | 11/1993 | Polin et al. ................... 604/328 |
| 5,509,888 | A | * | 4/1996 | Miller .......................... 600/29 |
| 6,091,992 | A | | 7/2000 | Bourgeois et al. |
| 6,124,523 | A | * | 9/2000 | Banas et al. ................. 623/1.15 |
| 6,395,026 | B1 | | 5/2002 | Aboul-Hosn et al. |
| 6,482,145 | B1 | * | 11/2002 | Forsell .......................... 600/30 |
| 6,491,623 | B2 | * | 12/2002 | Snyder et al. .................. 600/31 |
| 6,503,189 | B1 | * | 1/2003 | Forsell .......................... 600/29 |
| 6,675,809 | B2 | * | 1/2004 | Stack et al. .................. 128/898 |
| 6,770,024 | B1 | | 8/2004 | Rastegar et al. |
| 6,953,429 | B2 | * | 10/2005 | Forsell .......................... 600/29 |
| 7,037,343 | B2 | * | 5/2006 | Imran ....................... 623/23.65 |
| 7,141,071 | B2 | * | 11/2006 | Imran ....................... 623/23.64 |
| 7,338,437 | B2 | * | 3/2008 | Forsell .......................... 600/38 |
| 7,367,938 | B2 | * | 5/2008 | Forsell .......................... 600/40 |

(Continued)

OTHER PUBLICATIONS

International Preliminarty Examination Report of Aug. 10, 2005, International App. No. PCT/US03/41304.

(Continued)

*Primary Examiner* — Alvin J. Stewart
(74) *Attorney, Agent, or Firm* — Mahamedi Paradice Kreisman LLP

(57) ABSTRACT

An implantable digestive organ is provided for the transport of materials through the digestive tract and in one particular application to an artificial large bowel for replacing all or part of a colon or large bowel. The prosthetic organ of one embodiment includes an outer support structure, an expandable member or members located within the outer support structure, and a flexible inner member forming a conduit for the passage of material. The flexible inner member is located within the outer member and the expandable member or members are located between the inner member and the outer support structure. The expandable members are expanded and contracted, or inflated and deflated to provide a pumping action that pumps the material through the organ. The prosthesis may also include valves or sphincters at the entrance and/or exit points of the organ where material moves into and out of the prosthesis. An implantable pump unit may be included for inflating and deflating the expandable members according to a desired sequence.

9 Claims, 19 Drawing Sheets

U.S. PATENT DOCUMENTS

| | | | |
|---|---|---|---|
| 7,458,930 B2 * | 12/2008 | Meretei | 600/30 |
| 7,530,943 B2 * | 5/2009 | Lechner | 600/37 |
| 7,572,218 B2 * | 8/2009 | Schrag | 600/31 |
| 7,594,885 B2 * | 9/2009 | Byrum | 600/37 |
| 7,601,178 B2 * | 10/2009 | Imran | 623/23.65 |
| 7,648,455 B2 * | 1/2010 | Forsell | 600/30 |
| 7,775,966 B2 * | 8/2010 | Dlugos et al. | 600/37 |
| 2001/0020189 A1 | 9/2001 | Taylor | |
| 2003/0144708 A1 * | 7/2003 | Starkebaum | 607/40 |
| 2004/0034320 A1 * | 2/2004 | Burnett | 604/96.01 |
| 2004/0039452 A1 | 2/2004 | Bessler | |
| 2004/0107004 A1 | 6/2004 | Levine et al. | |
| 2006/0129237 A1 | 6/2006 | Imran | |

OTHER PUBLICATIONS

International Preliminarty Examination Report of Apr. 1, 2005, International App. No. PCT/US03/41305.

International Search Report of Jun. 24, 2004, International App. No. PCT/US03/41305.

International Search Report of Jun. 24, 2004, International App. No. PCT/US03/41304.

Non-Final Office Action mailed Jun. 23, 2010 in U.S. Appl. No. 12/558,473.

Written Opinion of Sep. 2, 2004, International App. No. PCT/US03/4130.

* cited by examiner

FIG._1

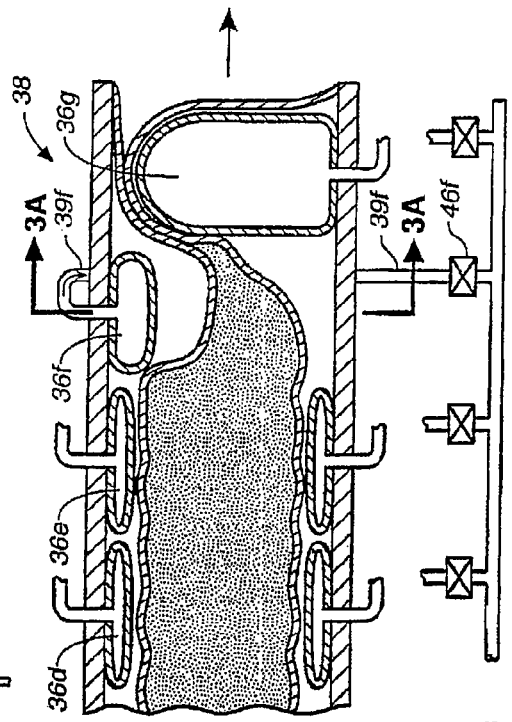
FIG._2C
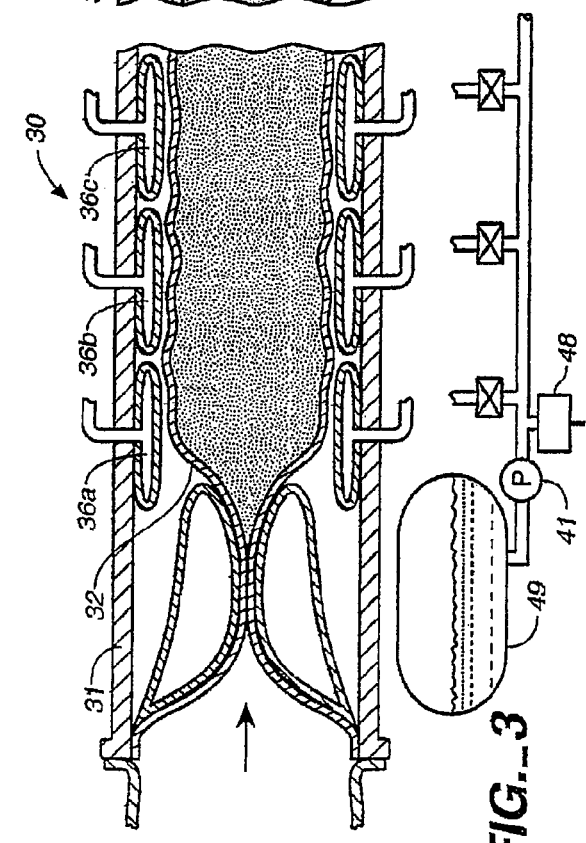
FIG._2B
FIG._2A
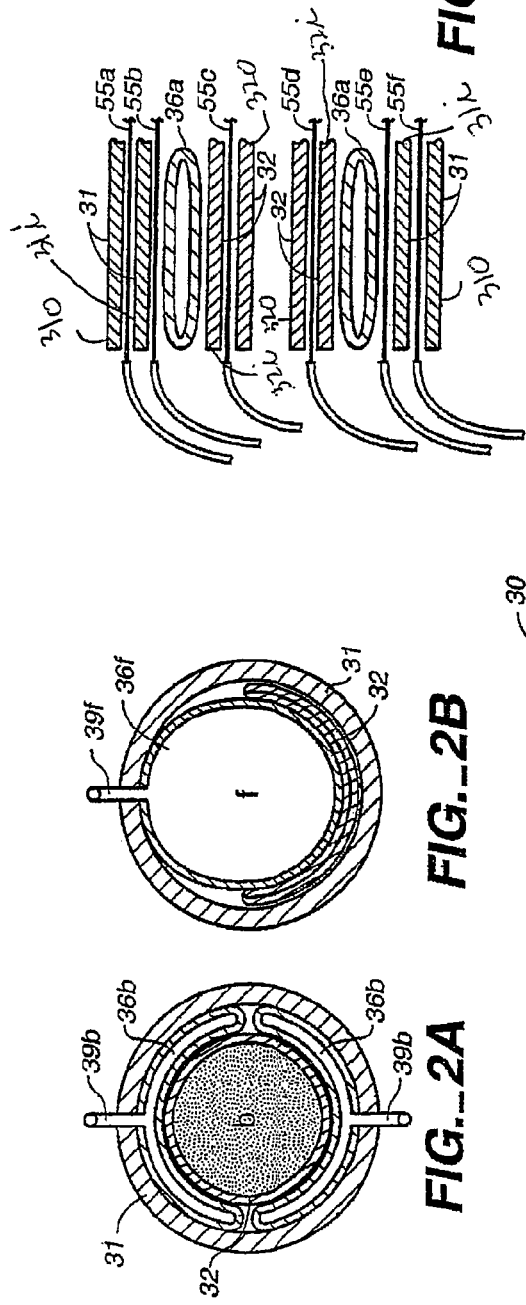
FIG._3

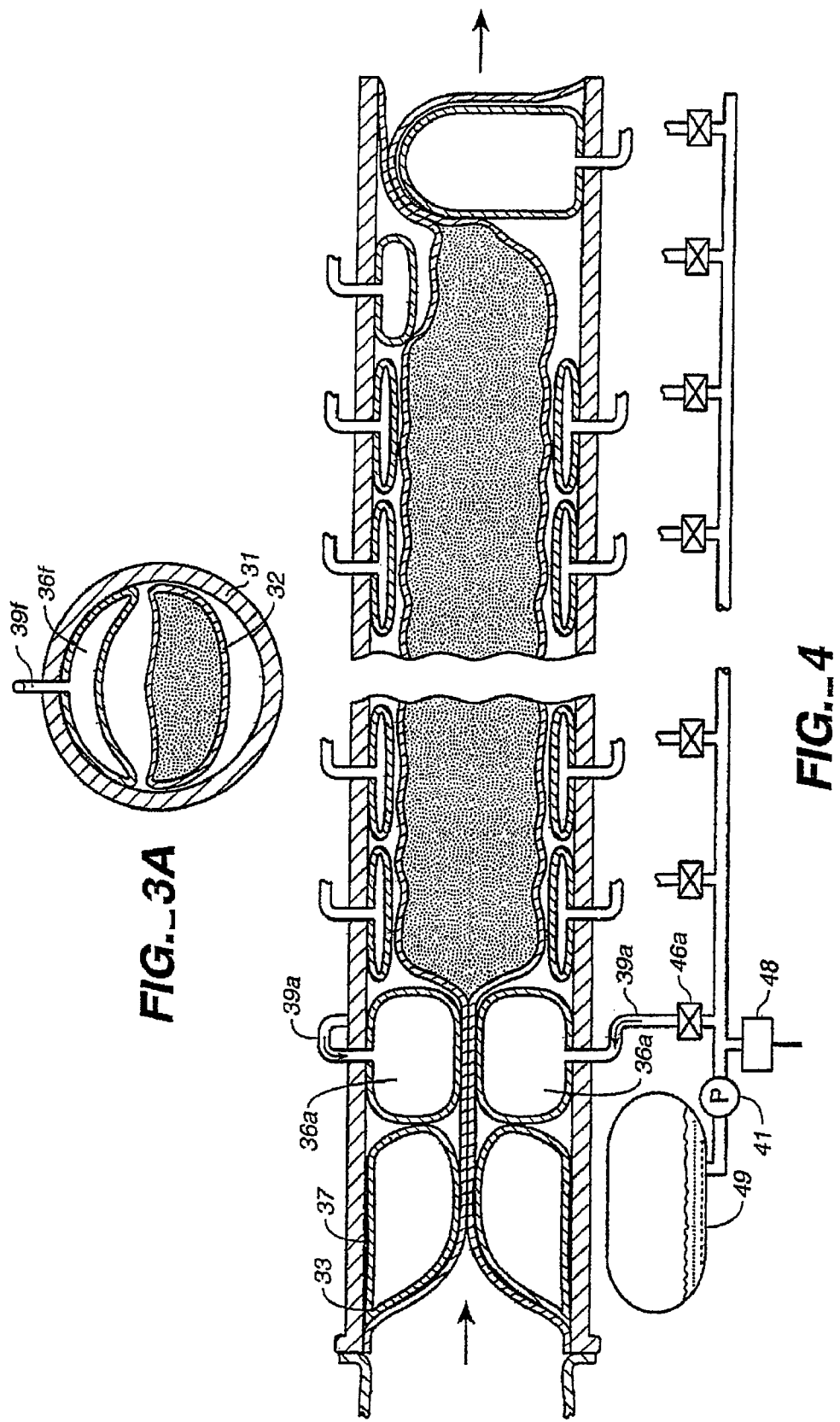
FIG._3A
FIG._4

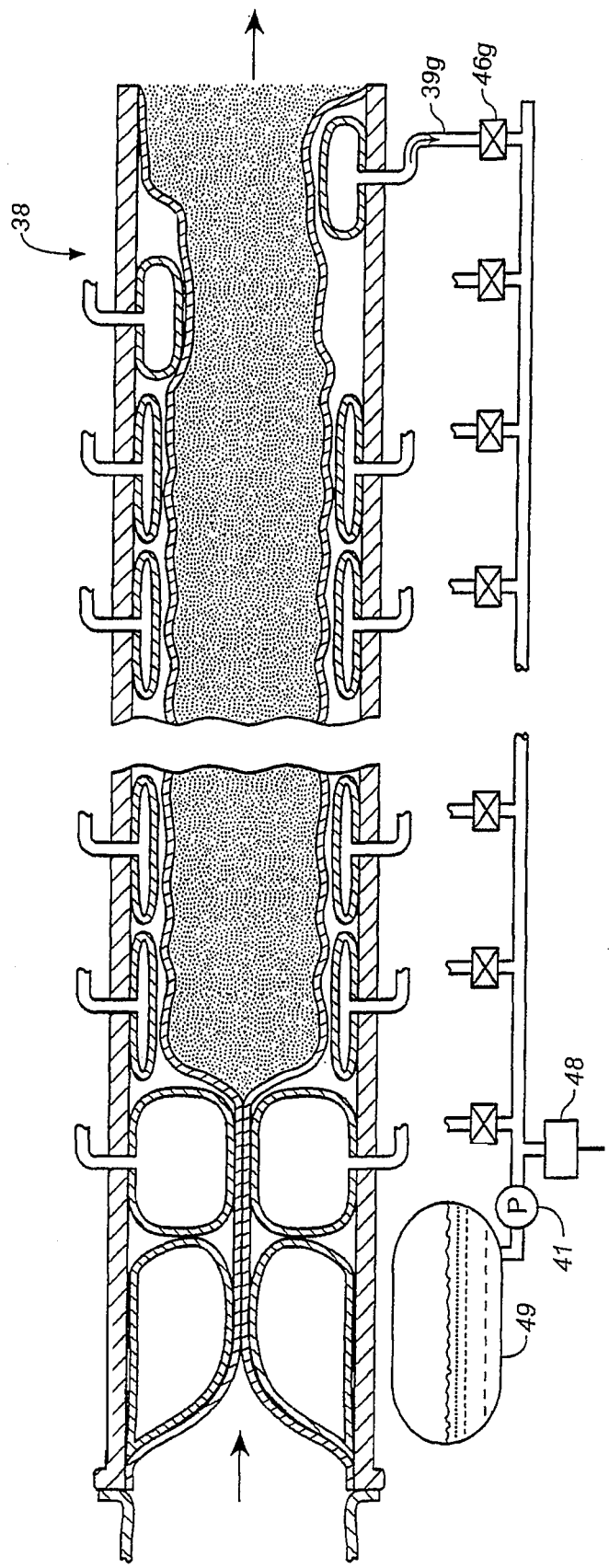
FIG._5

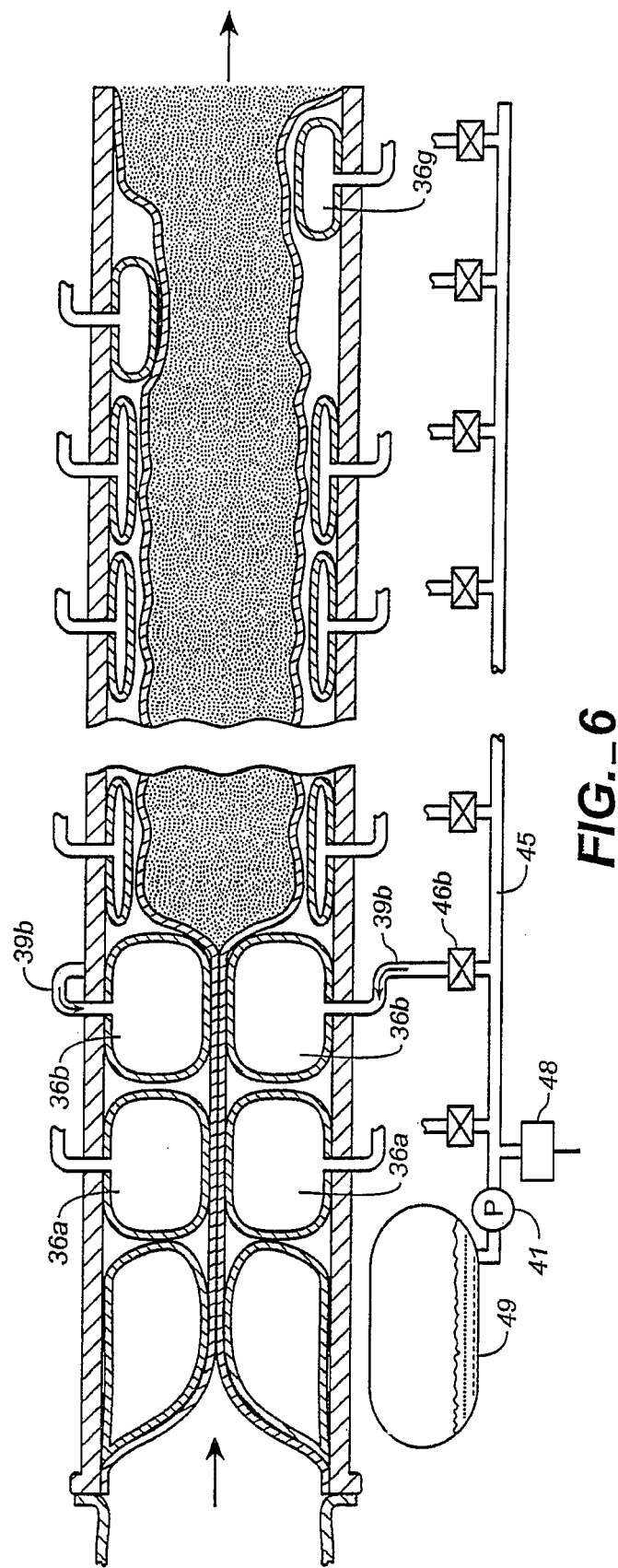
FIG._6

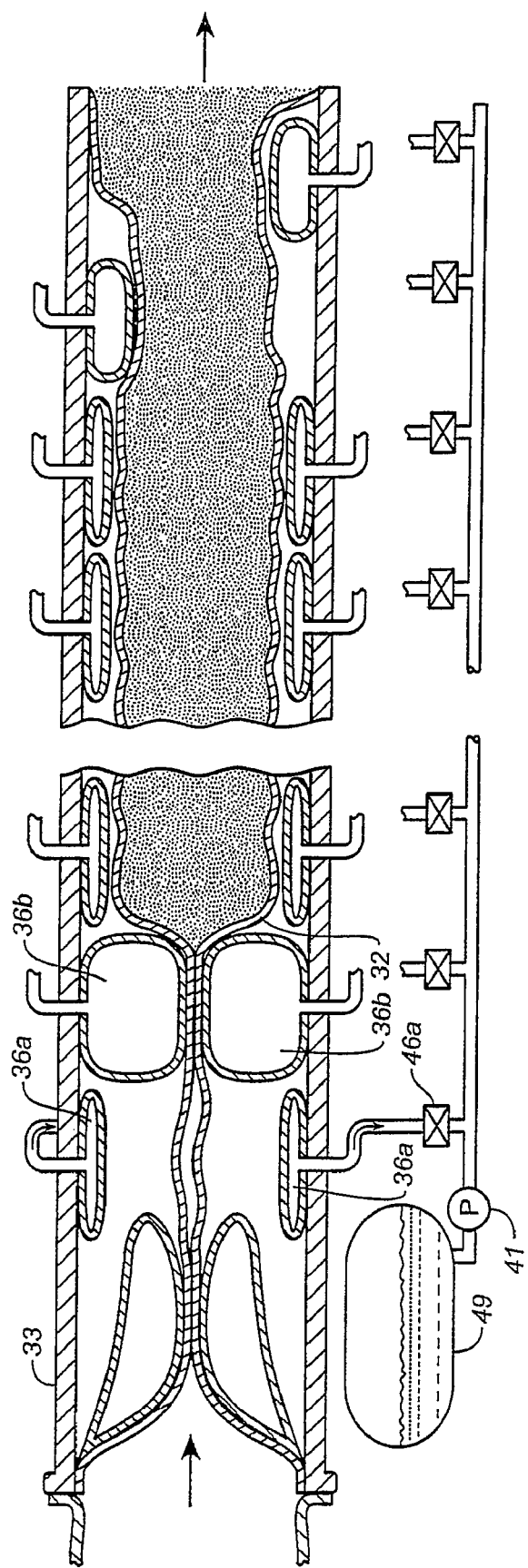
FIG._7

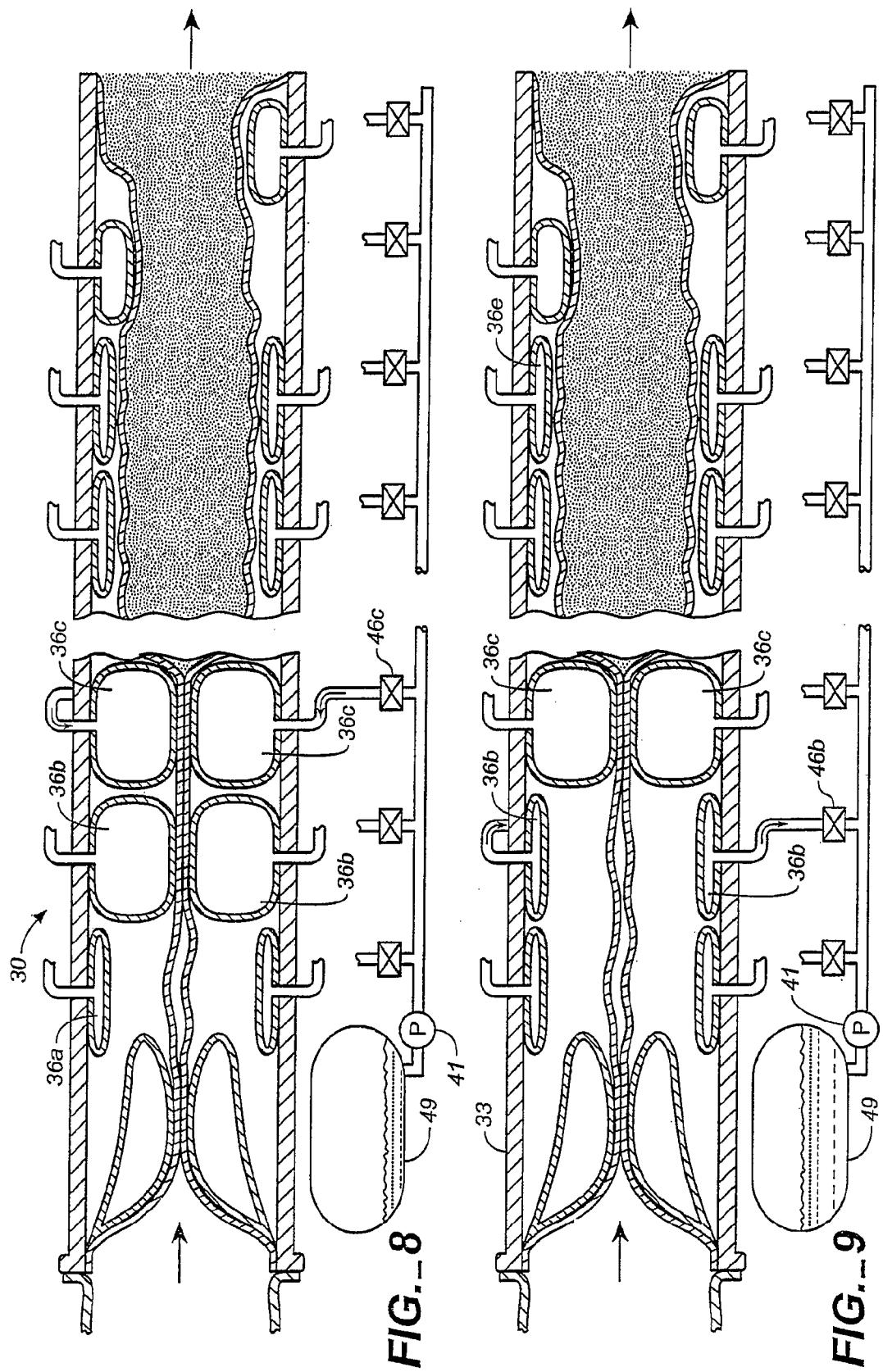
FIG._8   FIG._9

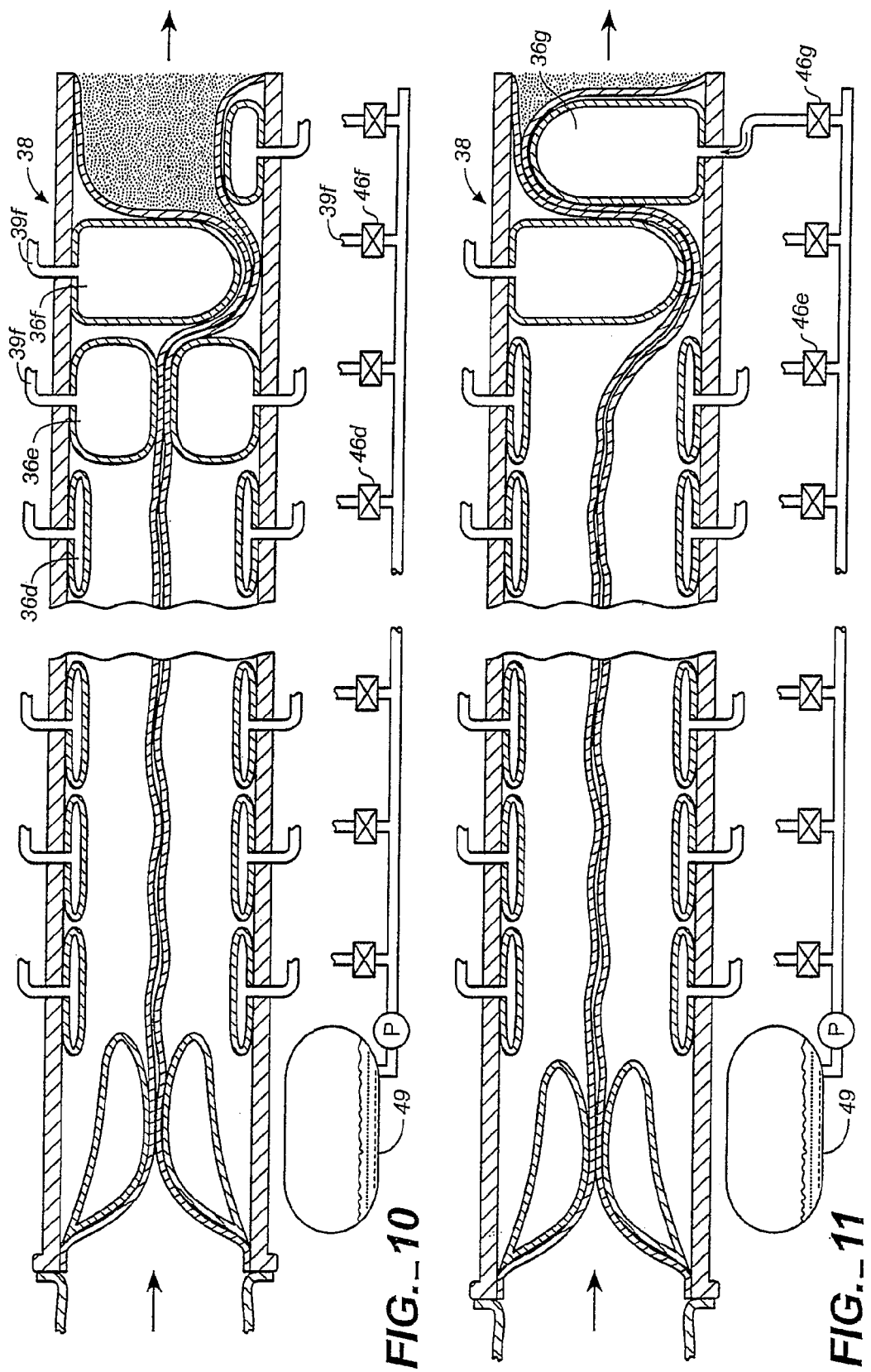

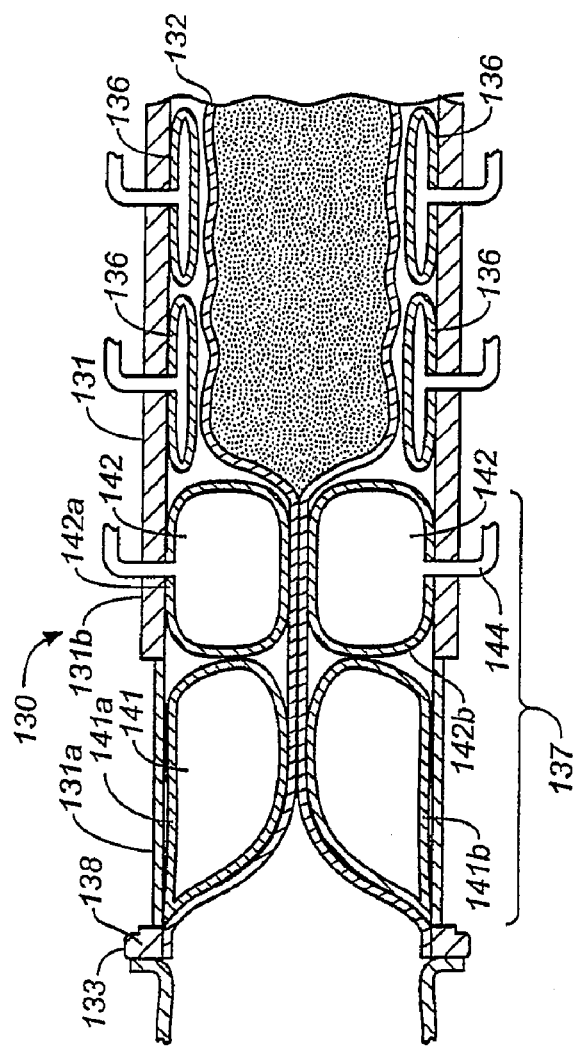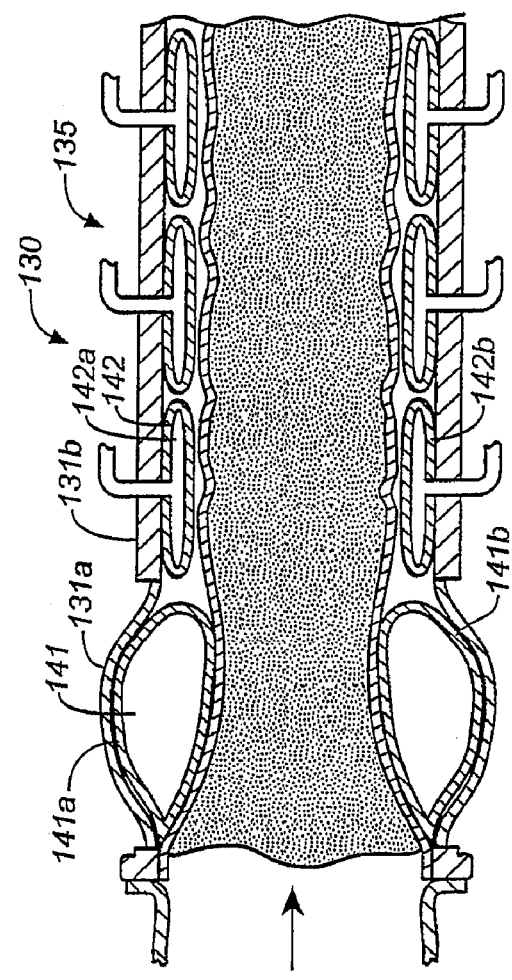
FIG._12A
FIG._12B

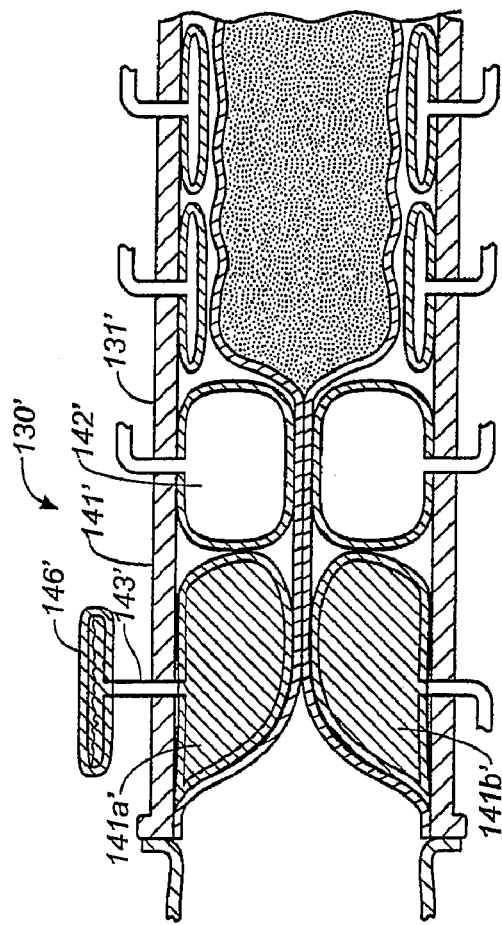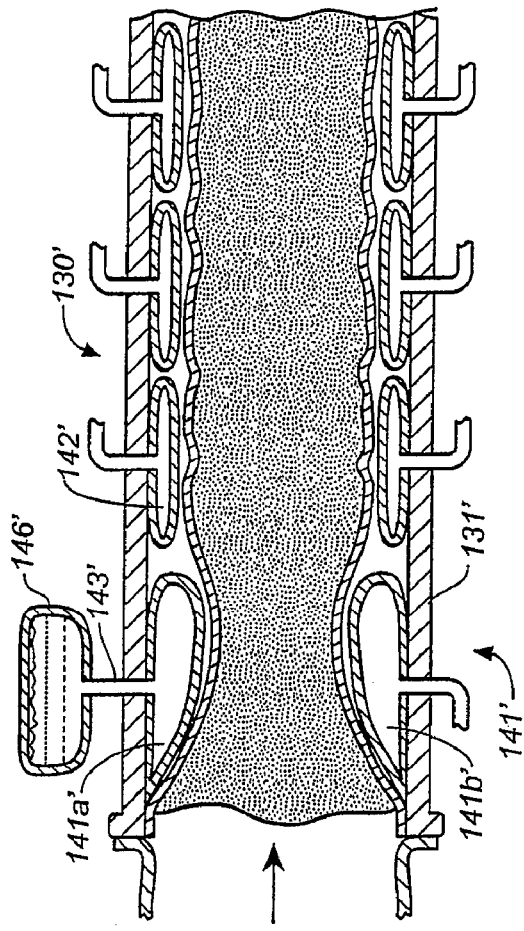

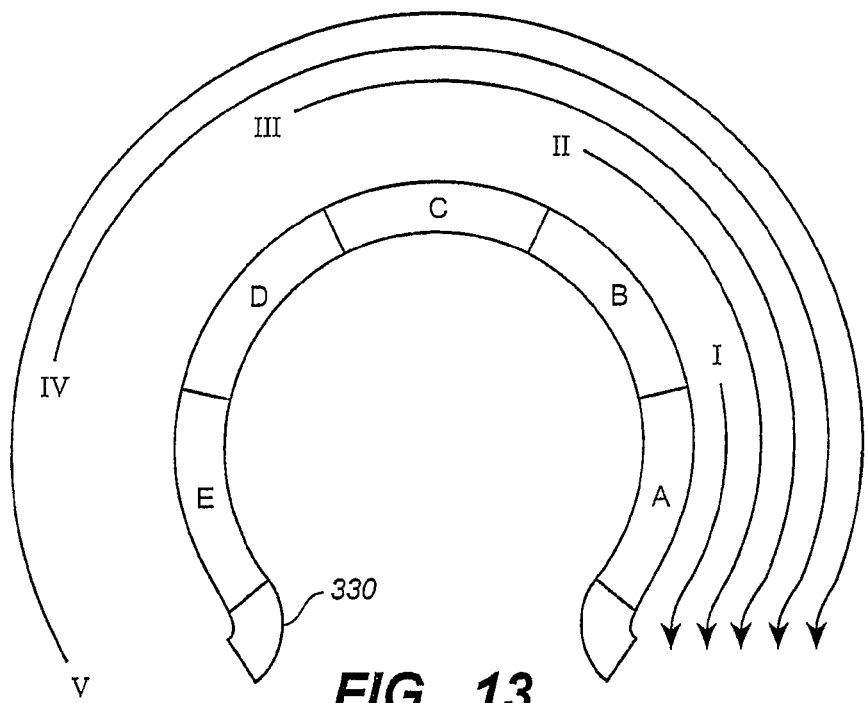
FIG._13
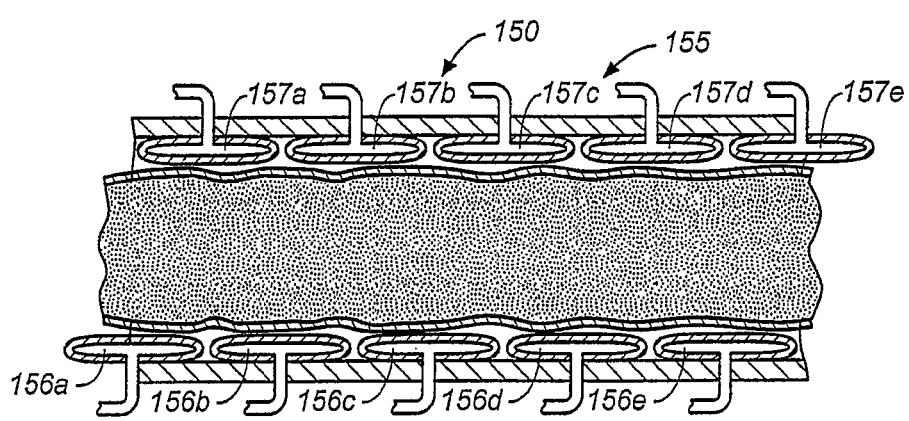
FIG._14
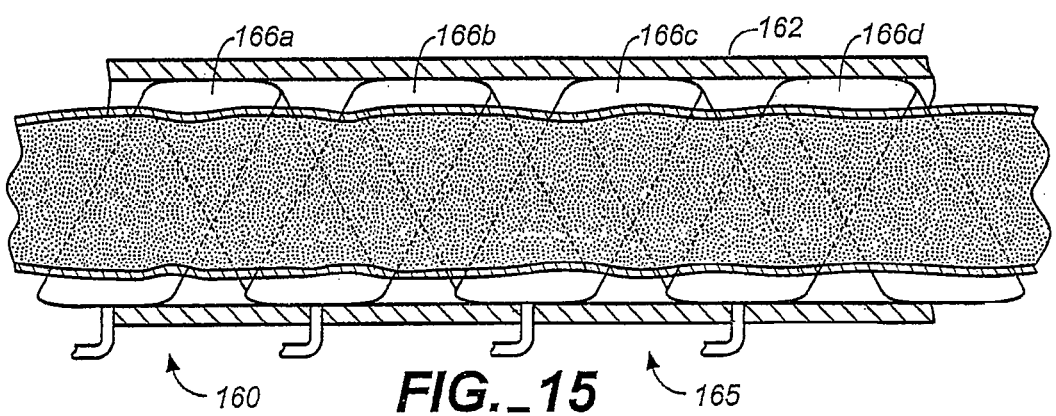
FIG._15

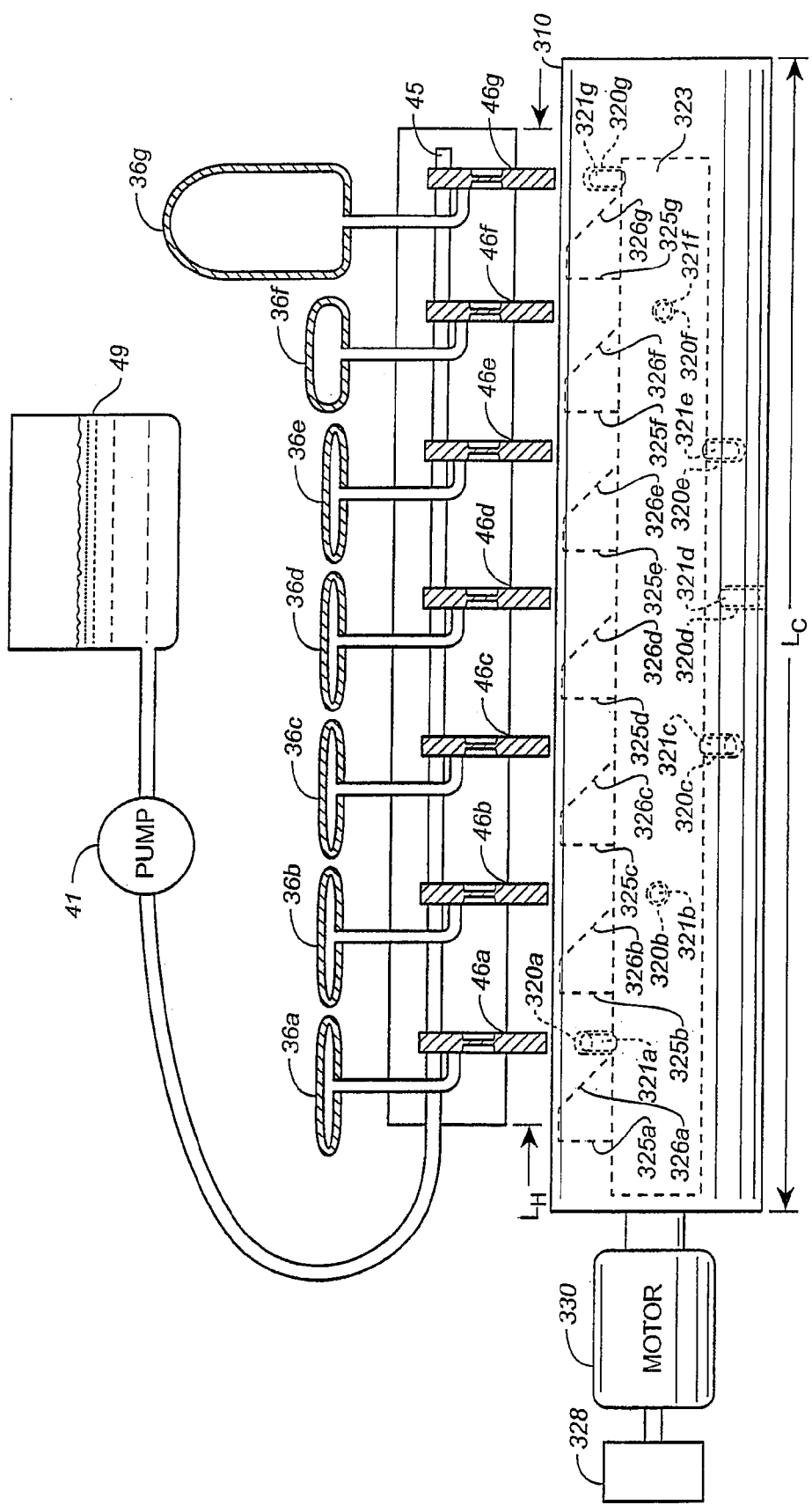
FIG._16

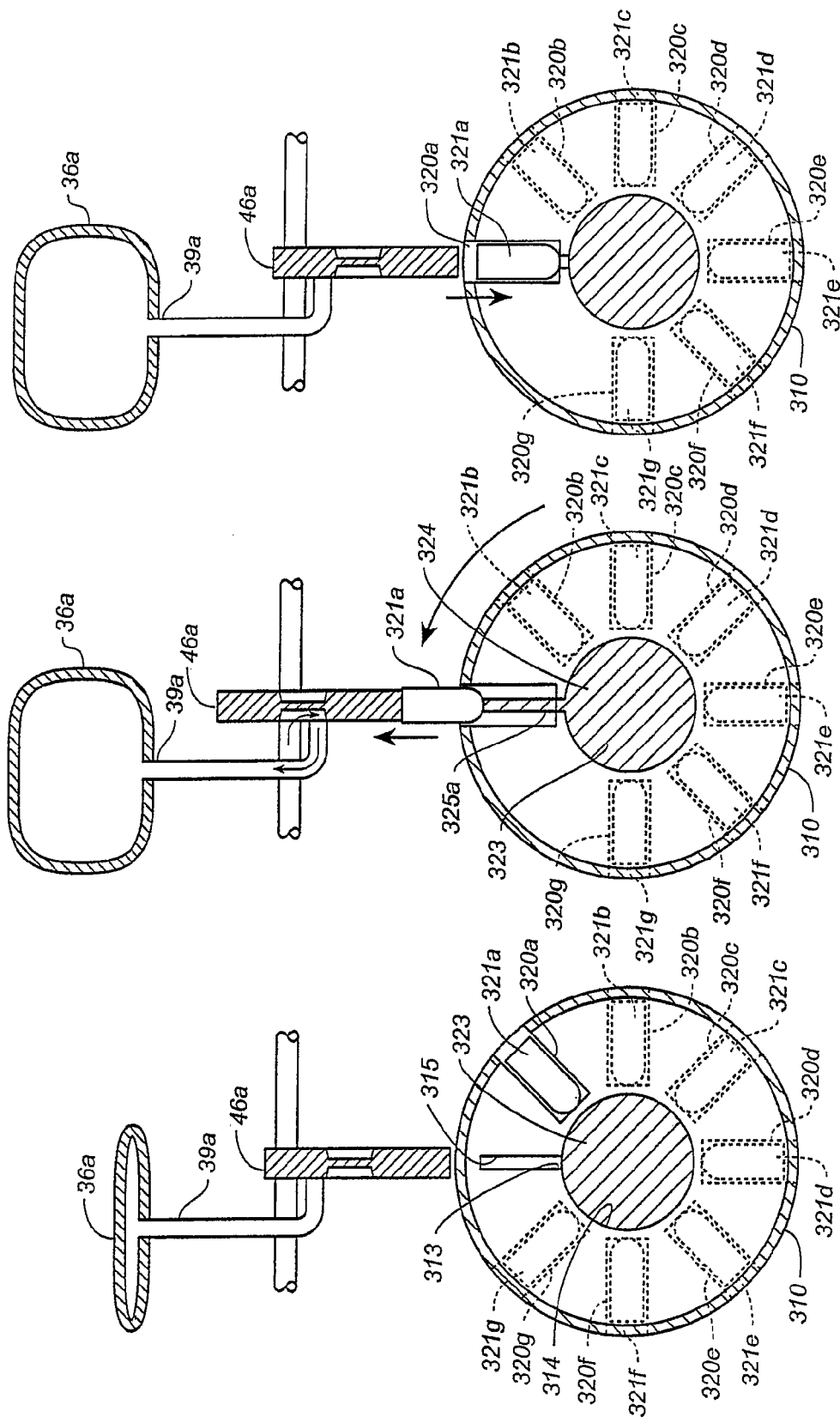

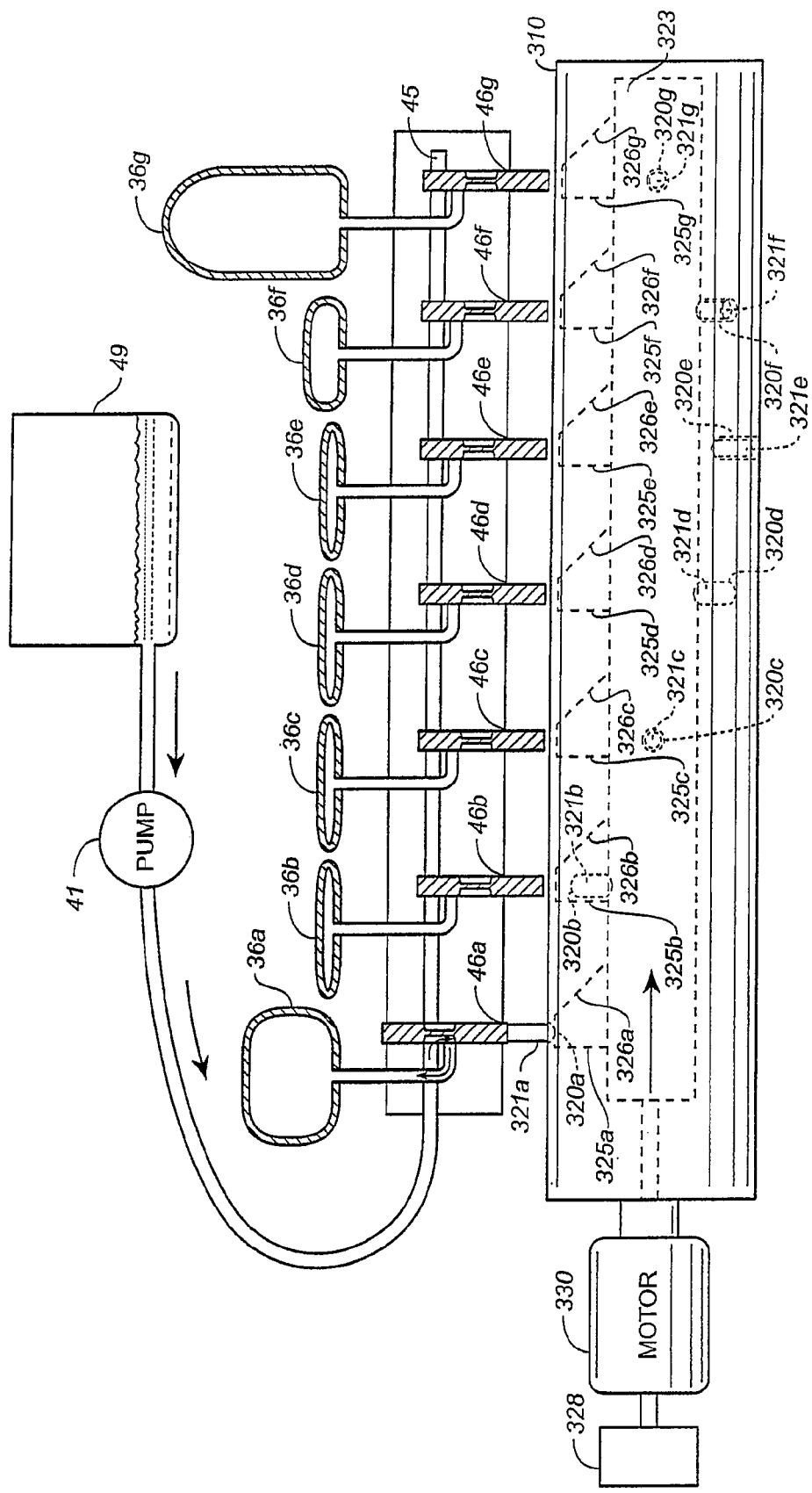
FIG._17

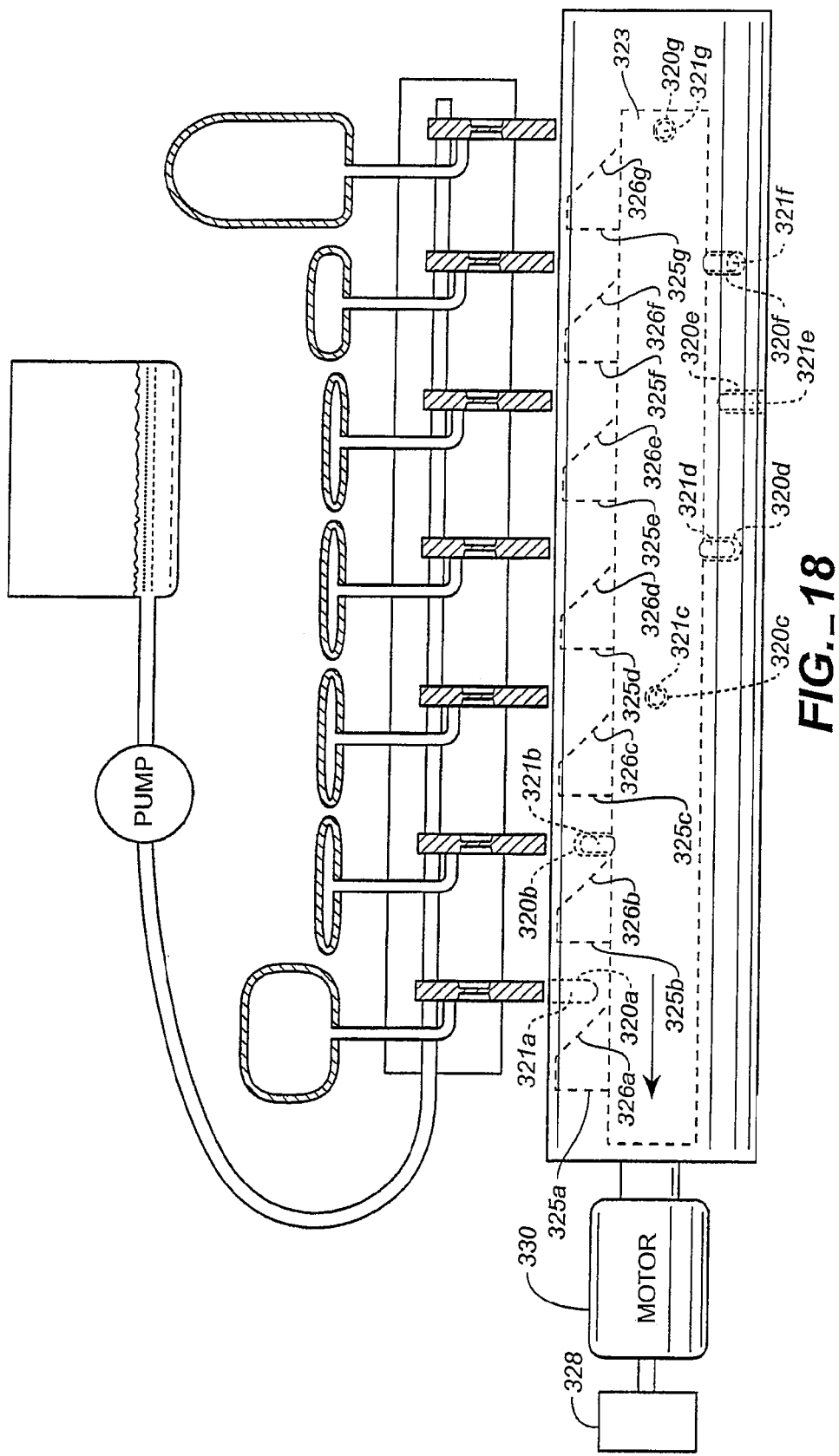
FIG._18

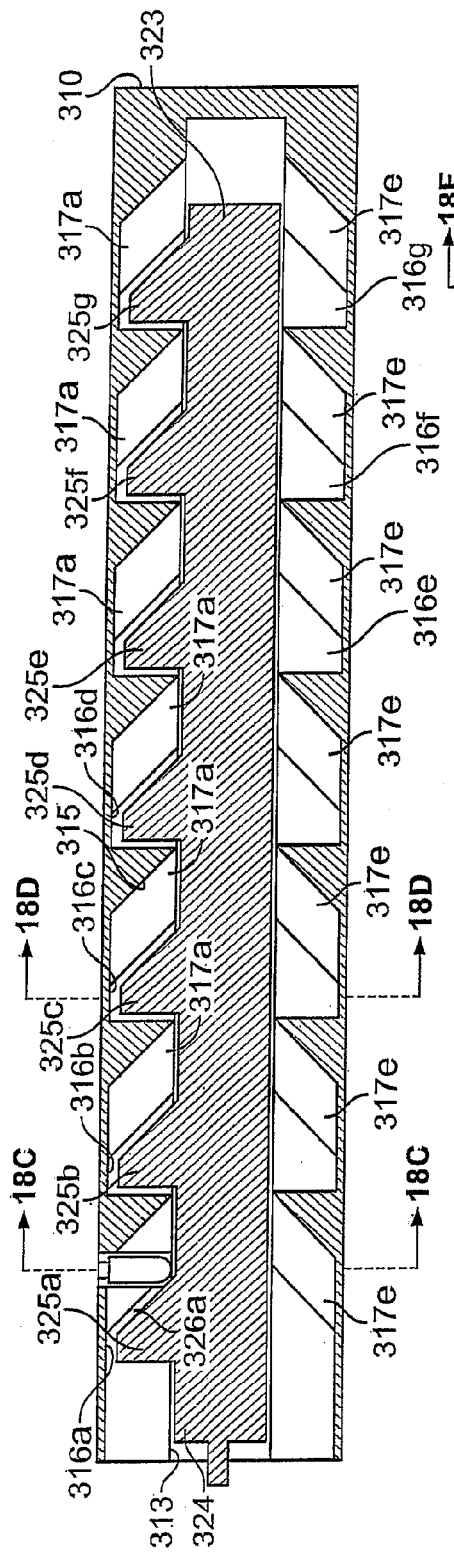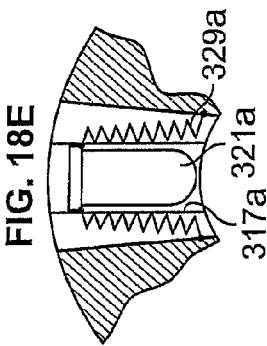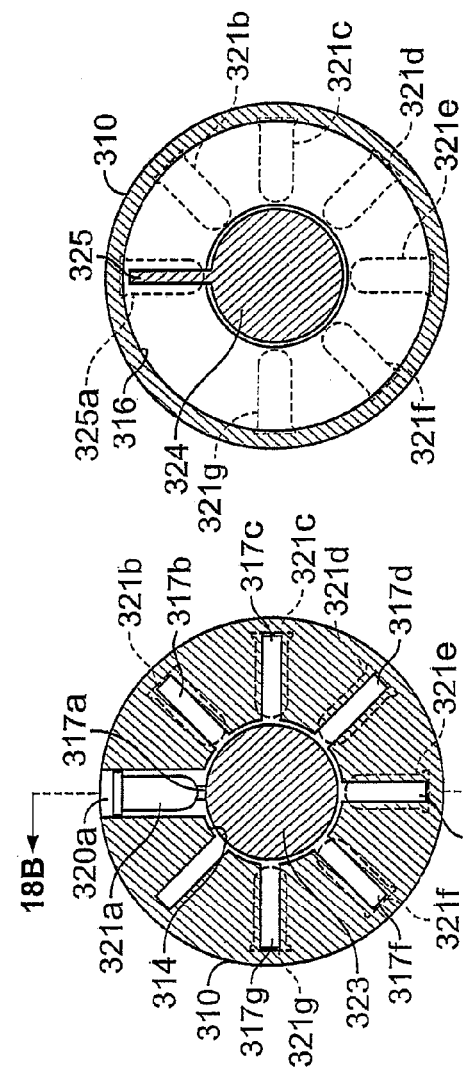

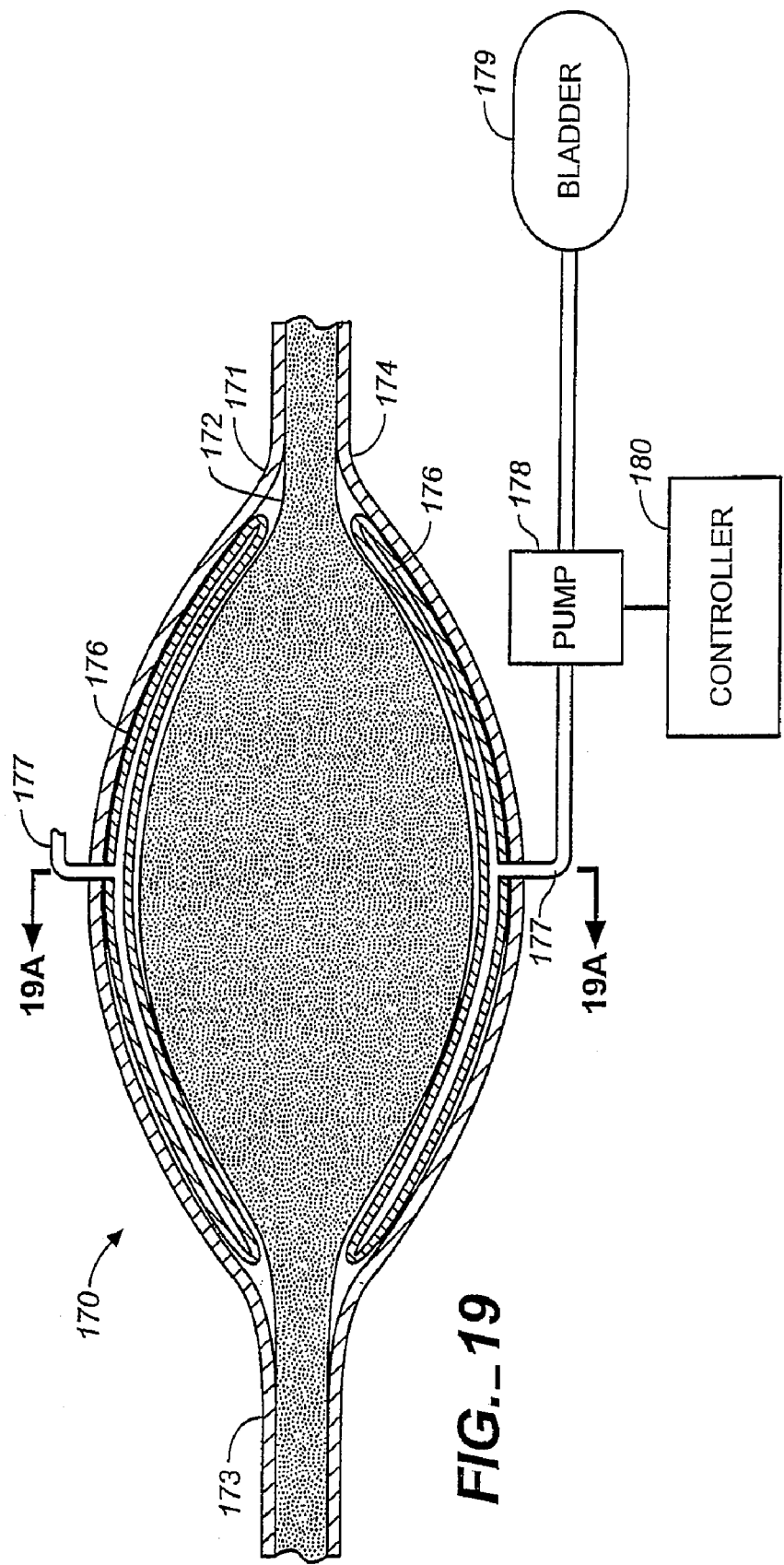
FIG._19

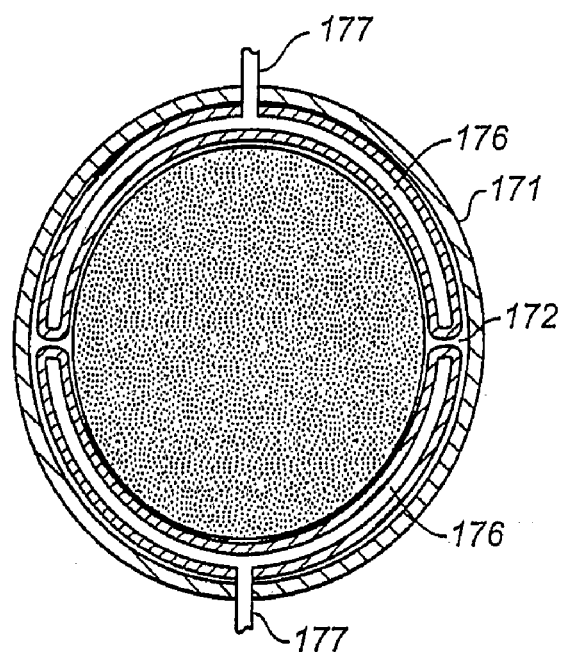
FIG._19A
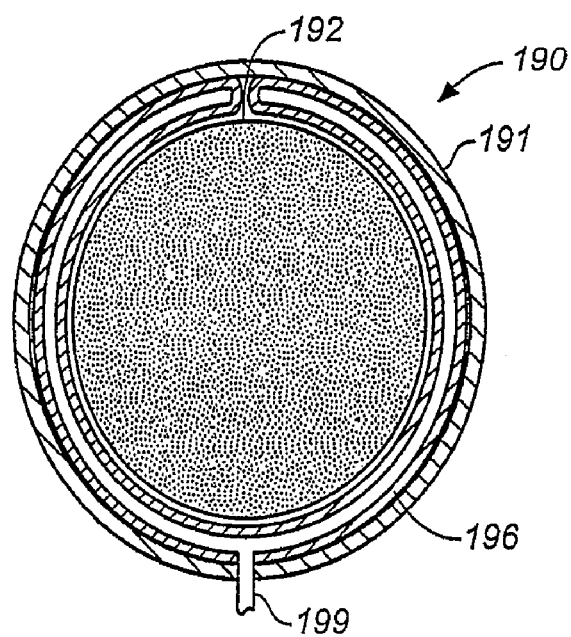
FIG._20

IMPLANTABLE DIGESTIVE TRACT ORGAN

CROSS-REFERENCE TO RELATED APPLICATIONS

This application is a continuation of U.S. patent application Ser. No. 10/328,446, filed 23 Dec. 2002, which is incorporated herein by reference in its entirety.

BACKGROUND OF THE INVENTION

1. Field of the Invention

The invention relates to an artificial organ for the transport of materials through the digestive tract and in one particular application to an artificial large bowel for replacing all or part of a colon or large bowel.

2. Description of the Related Art

A number of diseases or conditions are known to compromise the ability of peristaltic digestive organs of the body to function. These diseases or conditions may require resection of all or part of the organ. Such organs may include, for example, the stomach, intestines and bowel.

A number of diseases and conditions of the colon or bowel cause the colon or bowel to malfunction. In some situations such diseases or condition cause dangerous obstructions in the colon or bowel. In other situations, gastroparesis may result. Many of the diseases result in chronic or acute inflammation. As a result many diseases or conditions require removal of sections of the colon or bowel or a portion of the ilieum of the small intestine.

Crohn's disease is one example of an inflammatory bowel disease in which the inner lining of the bowel may become inflamed and cause obstructions in the bowel. Ulcerative colitus is another example of a disease of the colon characterized by ulcerations in the colon. Diverticulitis is a disease in which diverticulum of the colon become inflamed, trapping fecal material and potentially leading to obstruction, perforation or bleeding, with fecal material possibly leaking out into the abdomen. Diverticulitis in its most severe form may require resection of the affected portion of the bowel. Colon cancer, other obstructive growths may require significant portions of the bowel to be removed and in doing so may seriously compromise the functioning of the bowel. Another example of a colon/bowel diseases is toxic megacolon, where the colon becomes very large and may contain excessive amounts of feces at a given time.

As noted above, many diseases are treated with colonostomies or ileostomies, where all or a portion of the colon or ileum of the small intestine are removed. Many of these procedures require provision of an artificial stoma in the abdomen for emptying waste from the shortened functioning bowel. Often a pouch secured around the waist by a belt, is coupled to the stoma and is used to collect the waste. Mortality rates for the procedures remain high and for those successfully treated, the pouches are cumbersome to use and manage. Furthermore, the annual health maintenance costs for patients who have received this treatment is high.

Artificial sphincters have been proposed to replace failing sphincters. Typically theses devices are cuffs to be placed around the outside of an organ to control the opening and closing of a stoma. Artificial sphincters may be used for example where fecal incontinence is present. This may occur in women as a result of childbirth.

Accordingly it would be desirable to provide a device and method for replacing all or part of the bowel including in some instances, the rectal sphincter.

SUMMARY OF THE INVENTION

The present invention provides an implantable prosthetic organ in which material is moved through the organ. In one embodiment the prosthetic organ moves material with peristaltic-like movement. The prosthetic organ includes an outer support structure, an expandable member or members located within the outer support structure, and a flexible inner member forming a conduit for the passage of material. The flexible inner member is located within the outer member and the expandable member or members are located between the inner member and the outer support structure. The expandable members are expanded and contracted, or inflated and deflated to provide a pumping action that pumps the material through the organ. The expandable members are isolated from the material moving through the prosthesis by the inner member in which the material is contained. Thus, the material avoids getting caught in the interstices around the expandable members.

The prosthesis may also include valves or sphincters at the entrance and/or exit points of the organ where material moves into and out of the prosthesis. These sphincters are also isolated from the material by the inner tube.

The organ is preferably an organ of the digestive system having an orad end through which the material enters and an aboral end out of which the material exits. The digestive organ of one particular embodiment comprises a prosthetic large intestine or bowel that replaces all or part of the large intestine or bowel. According to this embodiment, the outer member of the organ is a flexible tube. The prosthesis may include a valve or sphincter at the entrance (the orad end) and/or a rectal sphincter valve at the exit (the aboral end). A plurality of expandable members are arranged to be expanded in a sequence where the expandable members are expanded and contracted along the length of the prosthesis to provide a pumping action moving material through the organ. The prosthesis may work in sections that provide peristaltic movements according to a pattern or sequence of sections. For example an aboral section may be first actuated, followed by the adjacent section in the orad direction. The aboral section may then be actuated again. Thus, a build up of material and pressure from the entrance (orad end) to the end (aboral end) is avoided and the material is gradually moved through the organ.

The expandable members of one embodiment are balloons or inflatable members expandable with an inflation medium. The implantable organ further comprises an implantable pump system that includes a pump and a programmable controller. The implantable pump system in one embodiment also includes a reservoir of sterile inflation medium used to inflate the various expandable members. The reservoir may be implantable separate from the pump, e.g. in soft tissue. In general, the pump system is a closed system where the inflation medium is stored or passes through as it is pumped from one inflation member to another. Each expandable member may be configured in a number of manners in which the inflation of the expandable member causes the material in the inner tube to advance. For example, the expandable member may be configured as a plurality of opposing members that are inflated together through a common valve. Alternatively, the inflatable member may be in a doughnut type shape; or the inflatable member may also be staggered from other inflatable members such that together the inflatable members are in a spiral type configuration. Other patterns may also be used for the purpose of moving material through the inner tube. Preferably, each of the expandable members or groupings of expandable members has an input port and valve coupled to the pump such that a single valve is opened at a time. However, the system may alternatively have more than one valve open at a time.

The controller controls the inflation and deflation of the expandable members by controlling the opening and closing of the valves coupled to each of the expandable members, and by controlling the pump direction. In one embodiment, the inflatable members are inflated to a predetermined pressure. The pump may determine the inflation pressure by monitoring the pumping action or work of its motor. The inflation pressure may also be sensed by sensors that sense the pressure of the system, e.g. in the fluid header of the pump system. In one embodiment, the reservoir contains sufficient inflation medium to inflate two sections of expandable members (and if present, the rectal sphincter). According to one embodiment, a first section of expandable members corresponding to a first section of the tube is inflated, then a second adjacent section is inflated. The second section is inflated before the first section is deflated so that the material in the prosthesis cannot move back in an orad direction when the second section is inflated. The first section is then deflated. Then the fluid used to inflate the first section is then used to inflate the third section, etc. until each section is sequentially inflated.

The controller may also control selection of a section of the organ for the peristaltic movement. In this regard, sections may be selected according to a desired sequence of the section actuation. The controller may be preprogrammed to control the peristalsis pattern or may be reprogrammed externally or in response to sensed conditions at various locations in the bowel. For example the sensors may sense presence or absence of material in a section of the bowel and may direct a pattern of peristaltic movement in the various sections accordingly.

In one embodiment, a single electromechanical device actuates the opening and closing of the valves according to the sequence. The valve actuator selectively actuates a particular valve at a given time according to instructions from the controller.

The pump and the valve actuating mechanism may be powered through a coil inductively coupled transcutaneously to an external power source, or by a battery rechargeable through such coil and external power source. According to one embodiment, a user positions and actuates the external power source to evacuate the prosthesis. The electronics unit may be powered by a rechargeable or replaceable battery as the controller consumes relatively little power in its operation.

The implantable bowel may further include a rectal sphincter valve located at the aborad end of the organ. In one embodiment, the rectal sphincter valve includes expandable members configured to close the inner member into an S-shaped configuration. The S-shaped configuration tends to tighten and squeeze the inner member further closed when a pressure is applied at either end (orad or aborad) of the valve thus preventing leakage.

The implantable bowel may also include an orad valve located at the orad end. Preferably the orad valve is a one-way valve that opens to permit substance to enter into the inner member of the prosthesis while resisting backflow of material out of the organ in an orad direction through the orad valve. In the case of the colon replacement, the orad valve may replace the ileocecal valve. In one embodiment of the valve, a plurality of inflated members are inflated to a threshold pressure that when met permits movement of substance through the orad valve into the inner member of the prosthesis. The pressure is generally set to a typical threshold pressure that a small bowel exerts when it is contracting. In one embodiment of the orad valve, the inflated members are hinged at the orad end into the prosthesis so that when a pressure is applied from within the prosthesis tube, the hinged balloons tend to compress towards each other and further close the valve, preventing backflow of material. In another embodiment, the orad valve may include a combination of a low pressure valve and a high pressure valve where the low pressure valve permits the ingress of material into the prosthesis at a given external pressure, and the high pressure valve is selectively closed when the prosthesis is actively pumping material through it to prevent backward movement of the material into the small bowel.

The implantable prosthetic organ may also include a pressure sensor arranged to sense a pressure corresponding to a pressure within the inner member. The pressure sensor may sense a pressure that indicates to a user the bowel should be emptied, whether from material or gas filling the prosthesis. The pressure sensor is coupled to the controller, which has a telemetry coil arranged to communicate a telemetric signal with an external device. The controller is configured to communicate an alarm signal to the external device when a pressure sensed by the pressure sensor exceeds a threshold pressure. The external control device may communicate via telemetry with the controller, receive the alarm signal, and generate a user perceivable alarm in response to the alarm signal. Upon sensing the alarm, the user may activate the external control device which communicates to the controller to release material and/or gas from the device. The controller may also be programmed to gently, partially open the rectal sphincter to release gas, e.g. upon receipt of a telemetrically delivered user activated control signal.

BRIEF DESCRIPTION OF THE DRAWINGS

FIG. 2A is a cross section of FIG. 2 along the lines 2A-2A.

FIG. 2B is a cross section of FIG. 2 along the lines 2B-2B.

FIG. 2C is an enlarged view of a portion of the artificial large bowel of FIG. 2 illustrating the wire sensors.

FIG. 3 is a schematic of the artificial bowel of the embodiment of FIG. 2 during a first step of emptying the bowel in which the first inflation member of the rectal sphincter is deflated and the fluid is stored in the bladder.

FIG. 3A is a cross section of FIG. 3 along the lines 3A-3A.

FIG. 4 is a schematic of the artificial bowel of FIG. 2 during a subsequent step of emptying the bowel where a first inflation member is inflated with the fluid stored in the bladder.

FIG. 5 is a schematic of the artificial bowel of FIG. 2 during a further step of emptying the bowel where fluid is emptied from a second inflation member of the rectal sphincter.

FIG. 6 is a schematic of the artificial bowel of FIG. 2 during a further step of emptying the bowel where a second inflation member is inflated with the fluid stored in the bladder.

FIG. 7 is a schematic of the artificial bowel of FIG. 2 during a further step wherein the first inflation member is deflated.

FIG. 8 is a schematic of the artificial bowel of FIG. 2 during a further step wherein a third inflation member is inflated.

FIG. 9 is a schematic of the artificial bowel of FIG. 2 during a further step wherein the second inflation member is deflated.

FIG. 10 is a schematic of the artificial bowel of FIG. 2 during a further step wherein the last inflation member is in an inflated state and the first inflation member of the rectal sphincter is inflated.

FIG. 11 is a schematic of the artificial bowel of FIG. 2 during a further step wherein the last inflation member is in a deflated state and the second inflation member of the rectal sphincter is inflated closing the rectal sphincter.

FIG. 12A is a schematic of another embodiment of an orad valve of the invention in a first position.

FIG. 12B is a schematic of the orad valve of FIG. 12A in a second position.

FIG. 12C is a schematic of an alternative embodiment of a two stage valve in a first position.

FIG. 12D is a schematic of the two stage valve of FIG. 12C in a second position.

FIG. 13 is a schematic of an embodiment of the artificial bowel of the invention in which the bowel is divided into segments, and of a sequence of segmental peristalsis according to the invention.

FIG. 14 is a schematic side view of another embodiment of an artificial bowel of the invention.

FIG. 15 is a schematic side view of another embodiment of an artificial bowel of the present invention.

FIG. 16 is a schematic of a miniature valve-actuating device for controlling the valves of the pump of an embodiment of the invention in a first position with a valve closed and a rotational position in which none of the openings of the device are aligned with a valve.

FIG. 16A is an end view of the device as illustrated in FIG. 16 in the first position.

FIG. 17 is a schematic of the valve-actuating device of FIG. 16 in a second position.

FIG. 17A is an end view of the device illustrated in FIG. 17 with the valve open and an inflation being inflated.

FIG. 18 is a schematic of the micro valve-actuating device in the rotational position of FIG. 17 with the valve closed and the inflation member in an inflated position.

FIG. 18A is an end view of the device illustrated in FIG. 18.

FIG. 18B is a schematic side cross-section of the cylinder and rod of FIG. 18.

FIG. 18C is a cross section of FIG. 18B along the lines 18B-18B.

FIG. 18D is a cross section of FIG. 18B along the lines 18D-18D.

FIG. 18E is a top view of the cylinder of FIG. 18.

FIG. 18F is a cross section of a portion of the cylinder as illustrate in FIG. 18E along the lines 18F-18F.

FIG. 19 is a schematic of another embodiment of an artificial bowel of the present invention.

FIG. 19A is a cross section of FIG. 19 along the lines 19A-19A.

FIG. 20 is a schematic of a valve/sphincter of another embodiment according to the invention.

DETAILED DESCRIPTION

Figure 1:
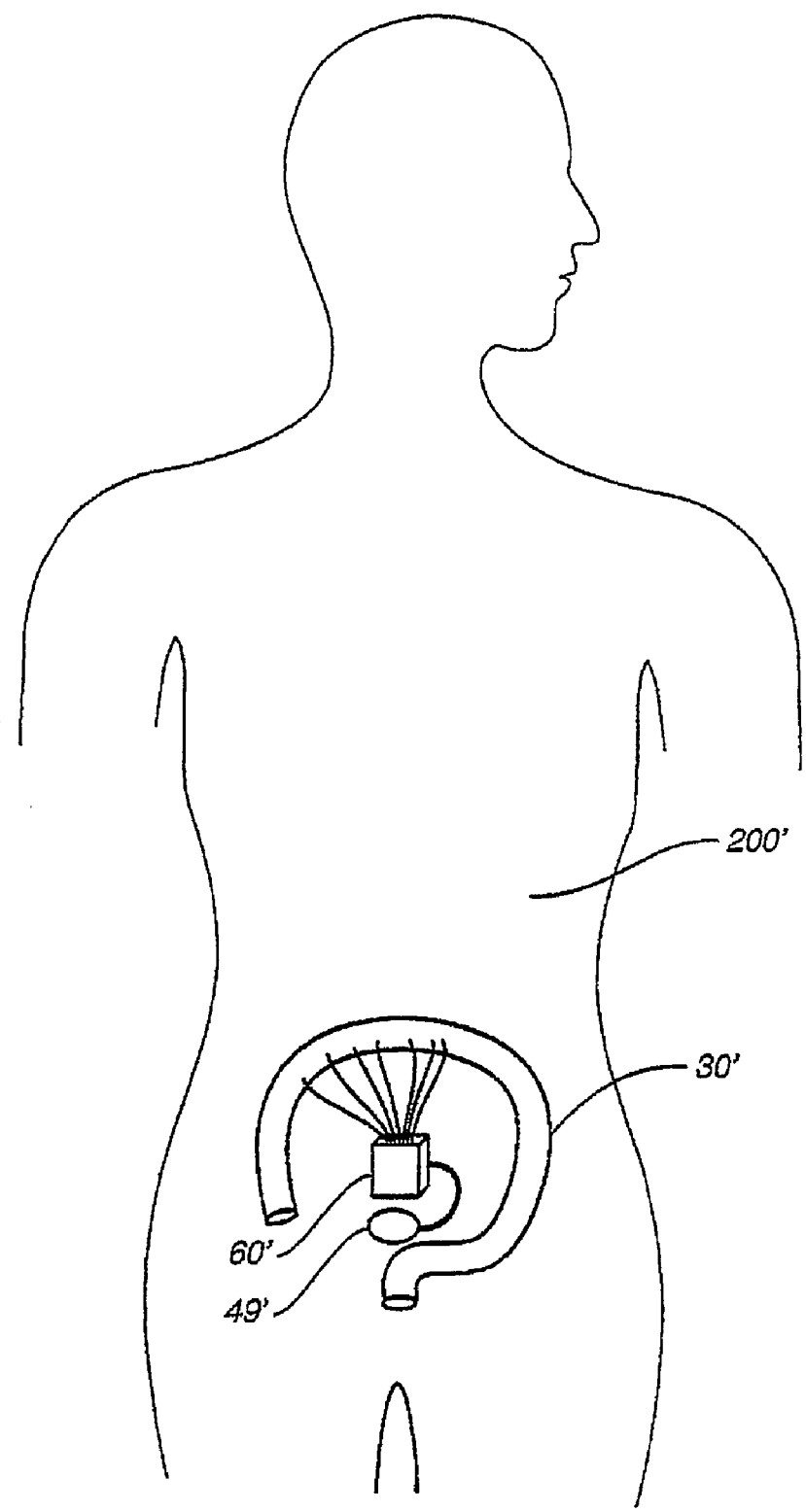
FIG. 1 is a schematic drawing of an implanted artificial large bowel according to an embodiment of the invention.

Referring to FIG. 1, according to one embodiment of the invention, a prosthetic large bowel 30' with a housing 60' including a hermetically sealed pump unit is implanted in a patient's abdomen 200'. The housing 60' may also include a controller for controlling the pump and the prosthesis. The controller may also be implanted separately (in the abdomen or subcutaneously) or located externally of the patient's body, and coupled to the pump by an electrical connector. A bladder 49' for supplying inflation medium is implanted in the soft tissue and is coupled to the pump unit in the housing 60'. Alternatively, the bladder may be located with the pump unit. An electromagnetic coil for inductively receiving power from an external source may also be implanted subcutaneously and coupled to the pump.

A schematic of a prosthetic digestive tract organ of one embodiment is illustrated in FIGS. 2-11. The prosthesis includes a large bowel 30, a hermetically sealed pump unit 40 and a hermetically sealed electronics unit 50 including a controller 51 for controlling the pump unit 40. The pump unit 40 and electronics unit 50 may be contained in the same housing such as the housing 60' illustrated in FIG. 1 or may be separate.

The large bowel 30 includes an outer tube 31 which comprises an inner 31i and outer layer 31o of material, a series of inflatable member pairs 36a-e, an orad valve 37 an aboral valve or rectal sphincter 38, and an inner tube 32 comprising an inner layer 32i and outer layer 32o of material. If the rectal sphincter is functional or if a partial bowel replacement is desired, the rectal sphincter may not be necessary to provide in the prosthesis.

The outer tube 31 comprises a flexible, relatively inelastic material such as, for example, polyethylene or polyurethane, and provides structural support for the prosthetic bowel 30. However, an elastic material may also be used. The inflatable member pairs 36a-e form a bowel emptying mechanism 35. Hinged inflated members 37a, 37b located at the orad end portion 33 of the prosthetic bowel 30 form the orad valve 37. Inflatable members 36f and 36g form the rectal sphincter 38 at the aboral end portion 34 of the prosthetic bowel 30. The inner tube 32 comprises a thin-walled, non-elastic flexible material such as polyethylene or polyurethane. The inside of the inner tube 32 may be coated with an antibiotic surface, such as a silver coating, to reduce bacterial growth. The inner tube 32 is attached to the outer tube 31 at the orad end portion 33 and the aboral end portion 34 of the prosthetic bowel 30 (for example, by welding) to provide an isolated conduit through which material may pass. The orad end portion 33 of the outer tube 31 includes a relatively thicker portion for suturing the outer tube 31 to a small bowel or an orad section of the colon that is to remain intact. The inner tube 32 defines a lumen through which material may enter from the small bowel or small intestine and exit through the anus. The hinged members 37a, 37b forming the valve 37, the inflatable member pairs 36a-e forming the bowel emptying mechanism 35 and the inflatable members 36f, 36g forming the rectal sphincter 38 are located between the outer tube 31 and the inner tube 32. The inner tube 32 floats relatively loosely within the outer tube 31 so as to permit movement including the inflation and deflation of the inflatable member pairs 36a-e and inflatable members 36f, 36g.

The orad end portion 33 of the prosthetic bowel 30 is sewn onto the end of the small intestine, or in the case of a partial replacement of the bowel, the section of the bowel that is in communication with the small intestine. If the ileocecal valve is functional or in the case of a partial bowel replacement, the orad valve 37 may not be necessary for the prosthesis.

The orad valve 37 at the orad end portion 33 of the prosthetic bowel 30 is a unidirectional valve through which material may enter into the inner tube 32 for collection and ultimate excretion from the prosthetic bowel 30. The unidirectional feature of the valve 37 serves to prevent gas or substances from backing into the small intestine from the prosthetic bowel 30. In one application, the valve 37 may replace or augment the ileo-cecal valve between the small intestine and colon of a patient. The valve 37 comprises hinged members 37a, 37b coupled to the outer tube 31 at pivot locations 31a, 31b respectively and extending in an aboral direction from the pivot locations 31a, 31b to form a constricted passage through which material may pass into the prosthetic bowel 30. The hinged members 37a, 37b are anchored at the pivot locations 31a, 31b so that they can pivotally rotate within the outer tube 31, from the locations 31a, 31b. The inner tube 32 extends from the orad end portion 33 (where it is coupled to the outer tube 31) over the valve 37, so that materials passing through the prosthetic bowel 30 do not contact the valve 37, thus preventing materials from becoming lodged in interstices created by the hinged members 37a, 37b of the valve 37. In addition the hinged members 37a, 37b and inner tube 32 in combination form a valve-sealing surface. The hinged members 37a, 37b are inflated to a threshold pressure that is generally lower than that exerted by the small intestine when it is contracting to move materials into the bowel. Thus, when the small intestine is active and moving materials, a pressure is created that pushes the materials into the inner tube 32 through the valve 37. When pressure is created within the inner tube 32 from gases or the pumping action of the prosthetic bowel 30 (FIGS. 3-11), the hinged members 37a, 37b are pushed by the pressure, back in an orad direction, causing them to converge and close the valve 37. In this situation, the pressure within the prosthesis presses the inner tube 32 against the hinged members 37a, 37b, and resulting pressure on the hinged members 37a, 37b causes the valve 37 to close or tighten. In the illustrated embodiment, the hinged members 37a, 37b are inflated to a predetermined pressure.

The bowel emptying mechanism 35 comprises a series inflatable member pairs 36a-e attached to the inside of the outer tube 31 between the outer tube 31 and the inner tube 32 along the length of the prosthetic bowel 30. Although pairs 36a-e are illustrated, the number of pairs of inflation members depend on a selected prosthesis length and size of the inflation member pairs. According to one embodiment, the inflatable member pairs are approximately 1.5 inches long in an uninflated state, with about 16 pairs for a 24-inch long bowel emptying mechanism. The length of the prosthesis may vary from patient to patient depending on the size of the patient and the amount of bowel to be replaced. The inflatable members may also be longer or shorter.

Each inflatable member of a pair converges together when inflated, to move material through the prosthetic bowel 30. Each inflatable member pair 36a-e is coupled to and is in fluid communication with a corresponding one of conduits 39a-e, respectively. Conduits 39a-e are used to selectively deliver inflation medium to and from inflatable members 36a-e by an implanted pump unit 40.

The rectal sphincter 38 is located at the aborad end portion 34 of the prosthesis where the prosthesis is attached to the anus 202. The rectal sphincter 38 comprises inflation members 36f, 36g attached to the inside of the outer tube 31 between the outer tube 31 and the inner tube 32. The inflation members 36f, 36g are attached on opposing sides of the outer tube 31 from each other so that when inflated, the inflation members 36f, 36g direct the inner tube 32 around in an S-configuration and pinch the inner tube 32 closed. The S-shaped configuration closes the inner tube 32 in a manner such that if pressure is exerted from within the prosthetic bowel 30 against the inflation member 36f, it will cause the inflation member 36f to further seal together or approximate any gap between the inflation member 36f and the inflation member 36g, and pinch the inner tube 32 closed further between the inflation members 36f, 36g. As such, when the sphincter 38 is subject to increases in pressure, the possibility of stress incontinence will be reduced. The inflation members 36f, 36g are coupled by way of conduits 39f, 39g respectively to ports 35f, 35g in the header 45. The inflation members 36f, 36g may be selectively inflated or deflated by the pump unit 40 as described in more detail below. In this embodiment, two opposing inflation members are illustrated. However, additional opposing inflation members may be provided. Furthermore, although the inflation medium is described as being pumped to and from a reservoir into and out of the inflation members 36f, 36g and inflation member pairs 36a-e, in an alternative configuration, the inflation members 36f, 36g of the rectal sphincter 38 act as the fluid reservoir so as to preserve space.

Additionally, one or more of the inflation member pairs 36a-e may be partially inflated during the resting stage and may be periodically monitored by opening the corresponding valve and sensing the pressure with the pressure transducer 48. Accordingly, if pressure builds up from materials or gas, the controller 51 may provide an alarm or feedback signal telemetrically to an external device, which causes a user perceivable alarm. The user then may proceed to actuate the device for evacuation. In one embodiment in order to release gas, the external device may be actuated to deliver a control signal via telemetry to the controller 51, which in turn opens the rectal sphincter valve 38 by partially emptying the inflation members 36f, 36g by controlling the valves 46f, 46g and the pump 41. The pump 41 gradually and partially pumps fluid from the inflation members 36f, 36g to release gas. The pump 41 then pumps fluid back into the inflation members 36f, 36g.

Figure 2:
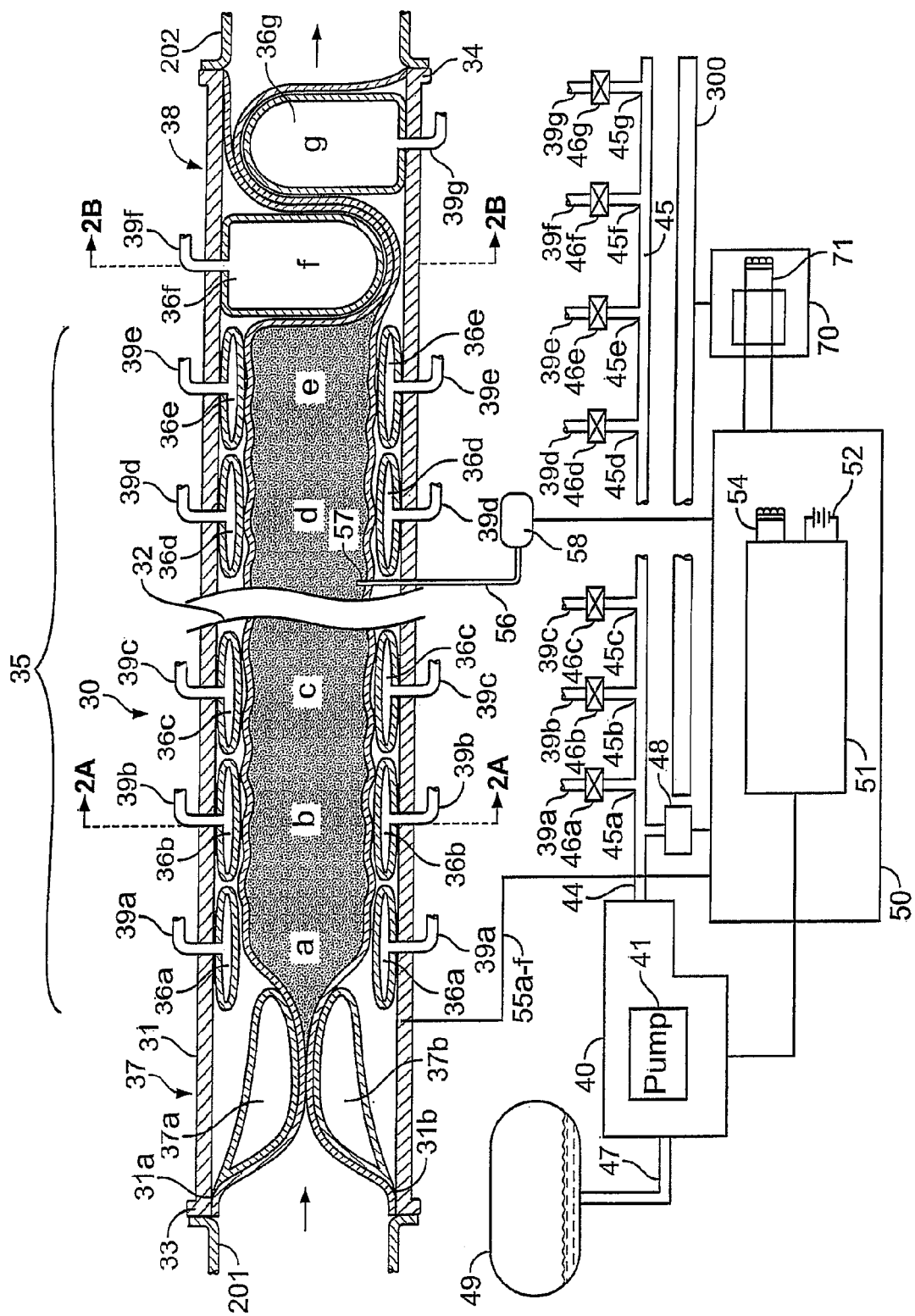
FIG. 2 is a schematic of an artificial large bowel, pump, valve actuator and controller of an embodiment of the invention in a resting state.

As illustrated in FIG. 2, a controller 51 of an electronics unit 50 controls the implantable pump unit 40 to selectively inflate and deflate inflatable member pairs 36a-e and inflatable members 36f, 36g. The pump unit 40 includes a bi-directional hydraulic pump 41 having an intake 47 coupled to a fluid reservoir 49 and an output 44 in fluid communication with a header 45 having fluid ports 45a-g. The bi-directional pump 41 may be configured in a number of ways to provide pumping in two directions, for example, by controlling a series of valves that direct fluid into or out of the reservoir 49 or by providing a DC powered reversible pump. The fluid reservoir 49 contains a sterile, radiopaque inflation medium sufficient to inflate two pairs of inflation members 36a-e, two inflation members 36f, 36g or a combination thereof at a given time. The fluid reservoir 49 may be implanted at a location adjacent to or away from the pump unit 40 (e.g. in soft tissue).

Each fluid port 45a-g is coupled to a respective valve 46a-g, which is coupled to a respective conduit 39a-g. Each conduit 39a-g is coupled to a corresponding inflation member pair 36a-e or inflation member 36f, 36g. The valves 46a-g are controlled by a valve actuating device 300 which operation is controlled by an electronics unit 50 of the controller 51. The valves 46a-g in this particular embodiment are controlled by a electromechanical device described in more detail with reference to FIGS. 16-18F. Alternative valve actuating mechanisms are also contemplated, for example, individually operated bistable solenoid valves may be used.

A pressure transducer 48 is located between the output 44 of the pump 41 and the header 45. The pressure transducer 48 senses the pressure of the fluid of a particular section of inflation members when the corresponding solenoid valve of the corresponding port is in an open position. The pressure transducer 48 is coupled to the controller 51, which controls the pump 41 in response to a sensed pressure.

The electronics unit 50 includes a controller 51 and a battery 52 powering the controller 51. The controller 51 is programmed to control the action of the various elements of the prosthesis and to respond to various sensed conditions. The controller 51 is coupled to the pump unit 40 and controls when and in which direction the pump 41 is actuated. The controller 51 is also coupled to a valve-actuating device 300 that opens and closes the valves 46*a-g* according to a program stored in the controller 51, thereby sequentially inflating and deflating inflation member pairs 36*a-e* and inflation members 36*f*, 36*g*. According to one embodiment, only one valve is opened at a time. The controller 51 also includes a telemetry coil 54 for communicating information to and receiving information from an external device. The external device may be used to program operation parameters into the controller 51. The external device may also receive signals from the controller 51 or electronics unit 50 representative of various sensed conditions, e.g., pressure or system leaks. The external device may program or reprogram the controller 51 based on sensed parameters or other patient conditions. An external device may also power the pump 41 and the valve-actuating device 300 through an electronics unit 70 comprising an electromagnetic coil 71 for inductively receiving power from an external source. The electromagnetic coil 71 is coupled to the electronics unit 50 which included a voltage regulating circuit. The electronics unit 50 and controller 51 control the pump 41 by powering the pump 41 and by controlling the valve actuating device 300. The voltage regulating circuit in the electronics unit 50 operates to convert a high frequency AC signal to a regulated voltage signal that powers the pump 41 and valve actuating mechanism 300. Alternatively, coil 59 may be used for both powering the pump and electronics unit 50 and for bi-directional telemetry communication.

The prosthetic large bowel 30 is illustrated in FIG. 2 in an inactive position in which it is collecting waste material from the small bowel 201 to which it is attached at the orad end portion 33. In this position the rectal sphincter 38 at the aborad end portion 34 is in a closed position with inflation members 36*f*, 36*g* inflated. The inflation member pairs 36*a-e* of the bowel emptying mechanism 35 are relaxed and deflated. The orad valve 37 is free to open to permit the ingress of waste material when there is sufficient pressure in the small bowel 201.

The prosthetic bowel 30 also further includes wires 55*a-f* (FIG. 2C) embedded in the prosthetic bowel 30 along its length and communicating with the electronic circuit 50. The wires 55*a* and 55*d* are located in the outer tube 31 each between layers 31*i* and 31*o* and on opposing sides along the prosthetic bowel 30. Wires 55*b* and 55*e* are exposed between the inflation member pairs 36*a-e* and the outer tube 31 on opposing sides along the prosthetic bowel 30. Wires 55*c* and 55*f* are located in the inner tube 32 along the bowel 30 between layer 32*i* and 32*o*. Wire pairs 55*a* and 55*d* form an open circuit as do wire pairs 55*b* and 55*e*, and wire pairs 55*c* and 55*f*. The electronic circuit 50 is configured to sense a large drop in impedance in one or more of the pairs wires 55*a-f*, where a fluid closes the circuit of one or more of the wire pairs indicating potential leakage of fluid into, out of or within the bowel 30, e.g. from material external the prosthetic bowel 30, material passing through the inner member 32 of the bowel 30 or from an inflation member, or otherwise. In particular, a low impedance may be detected by the controller 51, which is configured to sense impedance changes in the wires 55*a-f*. The impedance of the pairs of wires 55*a-f* is periodically monitored by the controller 51. If a leak is detected a patient alarm may be triggered, e.g., by telemetrically delivering an alarm signal from the electronics unit 50 to an external device. Furthermore, the location or cause of the leak may be determined by which sires 55*a-f* have changed impedances. The wire pairs may be placed in different configurations within layers 31*i*, 31*o*, 32*i*, 32*o* or between the inner 32 and outer members 31, for example, they may be is parallel spiraled configurations to maximize the sensing of potential leaks.

The prosthetic bowel 30 also includes a conduit 56 through the prosthetic bowel 30, into a port 57 inside the inner tube 31 for receiving an antibiotic material from a reservoir 58. The reservoir 58 is coupled to the controller 51 and may include a pump controlled by the controller 51 that provides a periodic or otherwise actuated (e.g. by a patient) injection of antibiotic material or gas dissolving material into the inner tube 32.

FIGS. 3-11 illustrate a sequence of emptying the bowel 30 of one embodiment of the invention. In FIG. 3, the inflation member 36*f* of the rectal sphincter 38 is emptied through the conduit 39*f* by opening valve 46*f*. The pump 41 pumps the inflation medium out of the inflation member 36*f* and into the reservoir 49, which is then partially full. The valve 46*f* is then closed.

Next as shown in FIG. 4, the valve 46*a* is opened and the pump 41 pumps inflation medium from the reservoir 49 into the inflation member pair 36*a* through the conduit 39*a*. The inflation member pair 36*a* is inflated to a predetermined pressure as sensed by pressure transducer 48 or alternatively as sensed by the motor. Once the inflation member pair 36*a* is inflated, the valve 46*a* is closed by the valve actuating mechanism 60 (FIG. 2). Inflation of the inflation member pair 36*a* closes the valve 37 on the orad end portion 33 due to the pressure from the inflation of pair 36*a*. Waste material is moved in an aborad direction within the inner tube 32, due to the mechanical movement of the inflation member pair 36*a* and any pressure gradient resulting therefrom.

Next, as shown in FIG. 5, the rectal sphincter 38 is completely opened by opening the valve 46*g* and pumping the fluid from the inflation member 36*g* through conduit 39*g* and into the reservoir 49. Thus material is permitted to exit through the rectal sphincter 38.

As illustrated in FIG. 6, inflation member pair 36*b* is next inflated to advance material through the prosthetic bowel 30. Before the adjacent inflation member pair 36*a* is deflated, the inflation member pair 36*b* is inflated by opening the valve 46*b* and inflating by pumping fluid from the reservoir 49 that was pumped out of the inflation member 36*g*, into inflation member pair 36*b* through conduit 39*b*. Thus, any materials are moved further in the aborad direction without allowing the material to move back in the direction of the inflation member pair 36*a*. The valve 46*b* is then closed.

Referring to FIG. 7, the valve 46*a* is selected again. The pump direction is reversed and the inflation medium is pumped out of the inflation member pair 36*a* and is returned to the reservoir 49. The orad end portion 33 of the prosthetic bowel 30 is isolated from the material moving through the inner tube 32 by the inflation member pair 36*b*. The valve 46*a* is then closed.

Referring to FIG. 8, inflation member pair 36*c* is next inflated to advance material further through the prosthetic bowel 30. Before the adjacent inflation member pair 36*b* is deflated, the inflation member pair 36*c* is inflated by opening the valve 46*c* and inflating by pumping fluid from the reservoir 49 into inflation member pair 36*c* through conduit 39*c*. Thus, any materials are moved further in the aborad direction without permitting the material to move back in the direction of the inflation member pair 36*b*. The valve 46*c* is then closed.

Referring to FIG. 9, the valve 46*b* is selected again, the pump direction is reversed and the inflation medium is pumped out of the inflation member pair 36*b* and is returned to the reservoir 49. The orad end portion 33 of the prosthetic bowel 30 is isolated from the material moving through the inner tube 32 by the inflation member pair 36*c*. The valve 46*b* is then closed. A number of inflation member pairs may be provided in the prosthetic bowel 30 and the sequence of inflating and deflating the inflation members continues until the last inflation member pair 36e is inflated.

As illustrated in FIGS. 10 and 11, after inflation member pair 36e is inflated and subsequently inflation member pair 36d is deflated, the remaining material is advanced through the rectal sphincter 38 and the sphincter 38 is closed by first inflating the inflation member 36f by opening valve 46f and pumping inflation medium from reservoir 49 through conduit 39f. The inflation member pair 36e is deflated by opening valve 46e and pumping the inflation medium into the reservoir 49. (FIG. 10) The valve 46e is closed and valve 46g is opened and the inflation medium from the reservoir 49 is pumped into the inflation member 36g to close the valve 38.

This cycle of inflating and deflating inflation members may be repeated in subsequent bowel emptying steps or sequences. The cycle may also be modified and the order of emptying along the length of the prosthetic bowel may be done is subsections according to a program, such as for example, as illustrated in FIG. 13. Referring to FIG. 13, a sequence of emptying of one embodiment is illustrated. According to the embodiment, a prosthetic bowel 330 is illustrated as being divided into five sections, Sections A-E with section A being the aborad most section coupled to the anus and section E being coupled to the small intestine. Each section includes a series of inflatable members such as, for example, the inflatable members of the prosthesis described with respect to FIGS. 2-11. As illustrated in FIG. 13, the sections of inflatable members are actuated in a sequence of sections. In the first sequence I, section A is actuated so that the inflatable members are inflated in a sequence in an aborad direction, excreting the material in section A.

After A is actuated, a second sequence II of inflatable member sections is actuated in which section B is actuated so that the inflatable members of section B are inflated in a sequence in an aborad direction and then section A is actuated inflating inflatable members of section A in an aborad direction. Thus, material is moved through sections B, then A and then is excreted.

A third sequence III of inflatable member sections is actuated in which section C is actuated, then section B is actuated and then section A is actuated. Thus material is moved through sections C, B, and A, and then is excreted. And similarly the fourth sequence IV of inflatable member sections is actuated with section D followed by Section C followed by section B and then followed by Section A. Finally a fifth sequence V of inflatable member sections is actuated with section E, followed by Section D, followed by section C, followed by Section B and followed by Section A. Thus, the prosthetic bowel 330 is emptied by first emptying the aborad most section and slowly working towards the orad end so that the pump does not have to pump the entire prosthetic bowel out at one time.

FIGS. 12A and 12B illustrate an alternative embodiment of a prosthetic bowel of the invention with a two stage orad valve. The prosthetic bowel 130 includes an outer tube 131, a plurality of inflatable member pairs 136, an inner tube 132 and an orad valve 137. The outer tube 131 comprises a first portion 131a constructed of a flexible, elastic material coupled to a second portion 131b constructed of a flexible, inelastic material. The inner tube 132 comprises a thin-walled, in-elastic flexible material such as polyethylene or polyurethane. Alternatively an elastic material may be used. The inside of the inner tube 132 may be coated with an antibiotic surface, such as a silver coating, to reduce bacterial growth. The inner tube 132 is attached to the outer tube 131 at the orad end portion 133 and the aborad end portion (not shown) of the prosthetic bowel 130 (for example, by welding) to provide an isolated conduit through which material may pass. The orad end portion 133 of the outer tube 131 includes a relatively thicker portion 138 for suturing the outer tube 131 to a small bowel or an orad section of the colon that is to remain intact. The inner tube 132 defines a lumen through which material may enter from the small bowel or small intestine and exit through the anus. The inflatable member pairs 136, located between the inner member 131 and the second portion 131b of the outer member form a bowel emptying mechanism 135. The number of inflatable member pairs 136 may be selected based on the desired length of the prosthetic bowel 130.

The orad valve 137, located at the orad end portion 133 of the prosthetic bowel 130 between the outer tube 131 and inner tube 132, comprises a first low pressure valve 141 and a second high pressure valve 142. The low pressure valve 141 includes two opposing inflated members 141a, 141b inflated to a predetermined pressure. The inflated members 141a, 141b are attached to the outer tube 131 and located between the inner tube 132 and the first portion 131a of the outer tube. The inflated members 141a, 141b tend to close together. (FIG. 12A) When a sufficient pressure or force is created in the small intestine from material moving from the small intestine into the prosthesis, the inflated members 141a, 141b open to permit the passage of material, pressing against the flexible elastic first portion of the outer tube 131 which expand under a threshold pressure. (FIG. 12B).

The high-pressure valve 142 is adjacent the low-pressure valve 141 in an aborad direction. The high-pressure valve 142 includes opposing inflatable members 142a and 142b located within the second portion of the valve 137. When inflated to a predetermined pressure, the inflatable members squeezes the inner tube 132 together preventing movement of material between the small intestine and the prosthetic bowel 130. To close the high-pressure valve 142, it is inflated by way of pumping fluid through conduit 144 with a fluid pump such as the pump 41 described with reference to FIGS. 2-11. Typically the high-pressure valve 142 is left open when the prosthetic bowel 130 is collecting materials from the small intestine (FIG. 12B). The high-pressure valve 142 is typically closed during or just prior to the bowel emptying mechanism 135 being actuated (FIG. 12A). The inflatable members 142a, 142b are inflated to a high pressure that can with stand the pressure of the bowel emptying mechanism 135 when it is actuated to move material through the prosthetic bowel 130. Alternatively or in addition, inflation members such as inflation member pairs 136 may be used as a high-pressure valve in the two-stage valve.

Alternatively, as illustrated in FIGS. 12C and 12D the inflated members 141a', 141b' are coupled through a conduit 143' extending from the inflated members 141a', 141b' out of the outer tuber 131', to an elastic bladder 146'. The outer tube 131' of the prosthetic bowel 130' is relatively inelastic. When a force exceeding a predetermined pressure is applied to the inflated members 141a', 141b', for example, by a pressure or by material entering the prosthetic bowel from the small bowel, a portion of the inflation medium within the inflated members 141a', 141b' is squeezed into the elastic bladder 146' (FIG. 12D). When the force is removed, the elasticity of the bladder 146' causes the bladder 146' to contract and squeeze the fluid out of the bladder back into the inflated members 141a', 141b' to its original resting state (FIG. 12C). Generally, the pressure of the low-pressure valve 141' is lower than or matches the pressure exerted by the small bowel when it contracts. Thus the low pressure valve remains closed unless a pressure is exerted on the orad side of the valve 141'. The valve 141' tends to close when a pressure is exerted from the aborad side in a similar manner as described with reference to FIGS. 2-11 above with respect to the valve 37. A high-pressure valve 142' operates in the same way as high pressure valve 142 described with reference to FIGS. 12A and 12B.

FIG. 14 illustrates an alternative configuration of inflatable members 156a-e and 157a-e of a bowel emptying mechanism 155 of an alternative embodiment of a prosthetic bowel 150. Upper inflatable members 156a-e are offset from the lower inflatable members 157a-e so that material is not stuck between opposing inflation member pairs. The inflatable members 156a-e, 157a-e may be inflated in a sequence similar to the sequence described above with respect to FIGS. 2-11 or alternatively each inflation member may be inflated in an aborad moving sequence.

FIG. 15 illustrates another configuration of inflatable members 166a-d of a bowel emptying mechanism 165 of an alternative embodiment of a prosthetic bowel 160. Each inflatable member 166a-d comprises an inflatable member wrapped in a spiral-like configuration around the inner circumference of the outer tube 162. The inflatable members 166a-d may be inflated in a sequence similar to the sequence described above with respect to FIGS. 2-11 and each inflation member may be inflated in an aborad moving sequence.

FIG. 19 illustrates an alternative embodiment of a prosthesis 170 of the invention. The prosthetic bowel 170 comprises an outer tube 171, and inner tube 172 and an inflation member pair 176 located between the inner tube 172 and the outer tube 171. Waste material enters the orad end portion 173, which is coupled to the small intestine (not shown), and exits the aborad end portion 174 which is coupled to the anus (not shown). A pump 178 is controlled by a controller 180 to pump fluid from a bladder 179 through a fluid conduit 177 and into the inflation member pair 176, and, visa versa to pump material out of the prosthetic bowel 170. The prosthetic bowel 170 may be used to replace the bowel or a small portion of the small or large bowel.

FIG. 20 illustrates an alternative configuration of an inflation member 196 to be used in a prosthetic bowel 190 wherein the inflation member 196 has a U-shape or a donut-like shape. The inflation member 196 is located between an outer tube 191 and an inner tube 192 and is inflated and deflated with an inflation medium through a conduit 199.

FIGS. 16-18F illustrate a valve-actuating device 300 according to an embodiment of the invention. The valve-actuating device 300 comprises a cylinder 310 having a length Lc aligned parallel with the length Lh of the header 45 of the pump 41 and adjacent the valves 46a-g. The cylinder 310 includes a plurality of openings 320a-g, spaced a defined distance along the length Lc of the cylinder 310 with respect to the other openings so that each opening is aligned lengthwise with a corresponding one of the valves 46a-g. Each opening 320a-g is also spaced a defined discrete distance circumferentially from the other openings. The cylinder 310 is coupled to a stepper motor 330 that rotates the cylinder 310 according to instructions from the controller 51 (FIG. 2) into discrete circumferential positions to interfacingly align a selected opening with a corresponding selected valve. Thus, the cylinder 310 may be rotated to discrete positions wherein in each position one of the openings 320a-g is interfacing a corresponding one of the valves 46a-g to be actuated.

A valve is actuated by a peg extending out of an interfacing opening in the cylinder 310 to engage and move the valve into an open position. Each opening 320a-g in the cylinder 310 includes concentrically moveable peg 321a-g respectively. Each of the pegs 321a-g is capable of being partially advanced in a circumferential direction out of the corresponding opening 320a-g in the cylinder 310. When interfacing with a corresponding valve 46a-g, a corresponding peg 321a-g may be advanced to engage and open the corresponding valve 46a-g to open it.

Once a valve is selected and the controller 51 instructs the stepper motor 330 to rotatably position the cylinder 310 accordingly, an actuating rod 323 is advanced through the cylinder 310 to engage and advance the corresponding aligned, interfacing peg out of the cylinder 310 to open the corresponding valve.

The actuating rod 323 slidably extends axially through an axial opening 313 in the cylinder 310. The rod 323 is coupled to a solenoid 328 that moves the rod 323 between two positions: a first resting position (FIG. 16-16A, FIGS. 18-18F) and a second valve actuating position (FIG. 17-17A). The solenoid 328 advances and retracts the rod 323 to and from a valve actuating position. The actuating rod 323 moves in a direction generally perpendicular to the circumferential sliding direction of the pegs 321a-g. The actuating rod 323 includes a central rod 324 and a plurality of staggered fins 325a-g having cammed surfaces 326a-g. In the first position, the fins 325a-g are staggered in a lengthwise relationship between the valves 46a-g and a second position, the fins 325a-g are generally aligned in a lengthwise relationship with the valves 46a-g. The cammed surfaces 326a-g are arranged so that when the rod 323 is advanced to the second position, a corresponding one of the cammed surfaces 326a-g will engage a corresponding one of the pegs 321a-g to move the corresponding one of the pegs 321a-g circumferentially out of a corresponding one of the openings 320a-g.

The axial opening 313 through the cylinder 310 includes a central rod portion 314 for receiving the rod 323 and a fin portion 315 for receiving in the fins 325a-g. The central rod portion 314 extends axially through the cylinder 310. The fin portion 315 of the axial opening 313 includes open portions 316a-g staggered in a lengthwise relationship between the valves 46a-g. Each open portion 316a-g is open within the rod opening 313 about the circumference of the cylinder 310 so that when the rod 323 is in the first position, the cylinder 310 is fee to rotate without interference of the fins 325a-g. The fin portion 315 also includes a plurality of slits 317a-g wherein each slit extends longitudinally through the cylinder, between each of the open portions 316a-g and perpendicularly through a corresponding one of the openings 320a-g.

The fins 325a-g are aligned in a position with the circumferentially extending top portions facing the header 45. The cylinder 310 may be rotated when the rod 323 and fins 325a-g are in the first position. The cylinder 310 when rotated to one of its discrete positions aligns a corresponding slit with the fins so that in the second position the fins advance through that slit. When the fins 325a-g are moved into the second position, the fins 325a-g extend through the slit corresponding to the opening that is positioned in alignment with a corresponding valve. In each discrete position the fins 325a-g are aligned with a slit permitting the corresponding fin to slide into the opening and engage the pin moving the pin out of the opening engaging the correspond valve with which it is aligned, thus actuating the corresponding valve. Each peg 321a-g is biased by a corresponding spring (329a only is shown) into a position circumferentially into the opening so that when the fins are retracted (e.g. FIG. 18), the pin moves back into the opening.

The controller 51 controls the timing and actuation of the cylinder 310 rotation and the solenoid 328 positioning. Referring to FIG. 16, the cylinder 310 is rotated to a position in which none of the pegs are aligned with valve 36a. The rod 323 is in a first position in which the cylinder 310 may rotate freely. The cylinder 310 is then rotated as illustrated in FIG. 17 so that the opening 321a is aligned with the valve 46a. The rod 323 is advanced so that the fins 325a-g extend through the slit 317a. Fin 325a extends into the opening 320a that is aligned with the slit 325a and the cammed surface 326a of the fin 325a engages the peg 321a and advances it out of the opening 320a to actuate valve 46a. The valve 46a is opened and the pump 41 pumps fluid from the reservoir 49 into the inflatable member pair 36a. As illustrated in FIG. 18, the rod 323 is then retracted releasing the peg 321a, which is biased by spring 329a into the cylinder opening 320a, and the valve 46a is closed, leaving the inflation member pair 36a inflated.

While the invention has been described with reference to particular embodiments, it will be understood to one skilled in the art that variations and modifications may be made in form and detail without departing from the spirit and scope of the invention.

For example the peristalsis organ of the invention may be used in a prosthetic stomach organ or prosthetic pylorus such as, for example those disclosed in the U.S. application entitled "Stomach Prosthesis", filed on even date herewith, which is incorporated into this patent application by reference.

What is claimed is:

1. An implantable prosthetic digestive organ comprising:
    an elongate body having an orad end, an aboral end and a lumen therethrough, the elongate body configured to be implanted so as to replace at least a portion of a patient's bowel;
    at least one sensor which senses leakage of fluid into, out of, or within the elongate body;
    a bowel emptying mechanism coupled with the body which is capable of moving digestive material within the lumen from the orad end toward the aboral end; and
    a controller in communication with the mechanism for controlling the movement.

2. An organ as in claim 1, wherein the at least one sensor comprises an impedance sensor.

3. An organ as in claim 1, further comprising a reservoir for holding an injectable material and a pump configured to inject the injectable material into the lumen of the elongate body.

4. An organ as in claim 3, further comprising an injectable material wherein the injectable material comprises an antibiotic material, a gas dissolving material or a combination of these.

5. An organ as in claim 1, wherein the mechanism comprises a series of members disposed along the body which are capable of constricting the lumen in a manner so as to move the digestive material within the lumen from the orad end toward the aboral end; and
    wherein the members comprise inflatable elements which extend into the lumen upon inflation.

6. An implantable prosthetic digestive organ comprising:
    an elongate body having a first end, a second end and a lumen therethrough, the elongate body configured to be connected with a portion of a digestive tract of a patient so that the lumen is capable of receiving digestive material passing from the portion of the digestive tract;
    at least two inflatable members disposed along the body which are capable of extending into the lumen upon inflation and retracting from the lumen upon deflation;
    a pressure sensor configured to sense pressure within at least one of the inflatable members; and
    a pump connected with the inflatable members which causes the inflation and deflation due to actuation by a controller.

7. An organ as in claim 6, further comprising a controller and wherein the controller is capable of providing a signal to the pump in response to the sensed pressure.

8. An organ as in claim 6, further comprising a controller and wherein the controller is capable of receiving a control signal via telemetry.

9. An organ as in claim 8, further comprising an external device capable of transmitting the control signal in response to actuation by the patient.

* * * * *